United States Patent [19]
Germain et al.

[11] Patent Number: 5,948,409
[45] Date of Patent: Sep. 7, 1999

[54] T CELL RECEPTOR LIGANDS AND METHODS OF USING SAME

[75] Inventors: Ronald N. Germain, Potomac; Luigi Racioppi, Bethesda, both of Md.

[73] Assignee: The United States of America as represented by the Department of Health and Human Services, Washington, D.C.

[21] Appl. No.: 08/858,248

[22] Filed: May 19, 1997

Related U.S. Application Data

[62] Division of application No. 08/004,936, Jan. 15, 1993, Pat. No. 5,837,477.

[51] Int. Cl.$^6$ ..................................................... A61K 39/00
[52] U.S. Cl. ..................................... 424/193.1; 424/185.1; 435/7.24
[58] Field of Search .............................. 424/185.1, 193.1; 435/7.24

[56] References Cited

U.S. PATENT DOCUMENTS

| | | | |
|---|---|---|---|
| 5,260,422 | 11/1993 | Clark et al. | 530/403 |
| 5,284,935 | 2/1994 | Clark et al. | |

OTHER PUBLICATIONS

L. Racioppi et al, J. Immunol., 147, 3718–3727, 1991.
Alexander et al, J. Immunol. 150, 1–7, 1993.
De Magistris et al, Cell, 68, 625–634, 1992.
Evavold et al., Science, 252, 1308–1310, 1991.
Adorini et al., "In vivo competition between self peptides and foreign antigens in T–cell activation," Nature, 334, 623–625 (1988).
Adorini et al., "Competition for antigen presentation in living cells involves exchange of peptides bound by Class II MHC molecules," Nature, 342, 800–803 (1989).
Adorini et al., "Exogenous Peptides Compete for the Presentation of Endogenous Antigens to Major Histocompatibility Complex Class II–restricted T Cells," J. Exp. Med., 174, 945–948 (1991).
Ashwell et al., "Functional Analysis of the Interaction of the Antigen–specific T Cell Receptor With Its Ligands," J. Immunol., 136, 757–768 (1986).
Eckels et al. "Peptide–mediated modulation of T–cell allorecognition," Proc. Natl. Acad. Sci. USA, 85, 8191–8195 (1988).
Fiering et al., "Single cell assay of a transcription factor reveals a threshold activated by signals emanating from the T–cell antigen antigens receptor," Genes Dev., 4, 1823–1834 (1990).
Harding et al., "CD28–mediated signalling co–stimulates murine T cells and prevents induction of anergy in T–cell clones," Nature, 356, 607–609 (1992).
Letourneur et al., "T–cell and basophil activation through the cytoplasmic tail of T–cell receptor ç family proteins," Proc. Natl. Acad. Sci. USA, 88, 8905–8909 (1991).

Maryanski et al., "Synthetic Peptides as Antigens and Competitors in Recognition by H–2–restricted Cytolytic T Cells Specific for HLA," J. Exp. Med., 167, 1391–1405 (1988).
Matis et al., "Magnitude of response of histocompatibilty–restricted T–cell clones is a function of the product of the concentrations of antigen and la molecules," Proc. Natl. Acad. Sci. USA, 80, 6019–6023 (1983).
Metcalf et al.,"In Vito Tolerance Induction of Neonatal Murine B Cells, " J. Exp. Med., 143, 1327–1340 (1976).
Mueller et al., "An Accessory Cell–derived Costimulatory Signal Acts Independently of Protein Kinase C Activation to Allow T Cell Proliferation and Prevent the Induction of Unresponsiveness," J. Immunol., 142, 2617–2628 (1989).
Mueller et al., "Clonal Expansion Versus Functional Clonal Inactivation: A Costimulatory Signalling Pathway Determines the Outcome of T Cell Antigen Receptor Occupancy,:" Ann. Rev. Immunol., 7, 445–480 (1989).
Mueller et al., An Intracellular Calcium Increase and Protein Kinase C Activation Fail to Initiate T Cell Proliferation in the Absence of a Costimulatory Signal,: J. Immunol., 144, 3710–3709 (1990).
Murray et al., "Major histocompatibilty complex (MHC) control of CD4 T cell subset activation. II. A single peptide induces either humoral or cell–mediated responses in mice of distinct MHC genotype," Eur.J. Immunol., 22, 559–565 (1992).
Otten et al., Split Anergy in a CD8+ T cell: Receptor–Dependent Cytolysis in the Absence of Interleukin–2 Production,: Science, 251, 1228–1231 (1991).
Quill et al., "Stimulation of Normal Inducer T Cell Clones with Antigen Presented by Purified Ia Molecules in Planar Lipid Membranes: Specific Induction of a Long–Lived State of Proliferative Nonresponsiveness," J. Immunol., 138, 3704–3712 (1987).
Rock et al., "Selective Modification of a Private I–a Allostimulating Determinant(s) Upon Association of Antigen with an Antigen–presenting Cell," J. Exp. Med., 159, 1238–1252 (1984).
Rothbard et al., "Interactions Between Immunogenic Peptides and MHC Proteins," Ann. Rev. Immunol.. 9, 527–565 (1991).
Soloway et al., "Regulation of the Immune Response to Peptide Antigens: Differential Induction of Immediate–type Hypersensitivity and T Cell Proliferation Due to Changes in Either Peptide Structure or Major Histocompatibility Complex Haplotype," J. Exp. Med., 174, 847–858 (1991).
Townsend et al., "Antigen Recognition by Class I–restricted T Lymphocytes," Ann. Rev. Immunol., 7, 601–624 (1989).
Wegener et al., "The T Cell Receptor/CD3 Complex Is Composed of at Least Two Autonomous Transduction Modules," Cell, 68, 83–95 (1992).

Primary Examiner—David Saunders
Attorney, Agent, or Firm—Knobbe Martens Olson & Bear, LLP

[57] ABSTRACT

The present invention concerns TCR ligands with immunomodulatory properties, as well as methods of identifying such ligands and of using such ligands to modulate T cell effector responses.

11 Claims, 12 Drawing Sheets

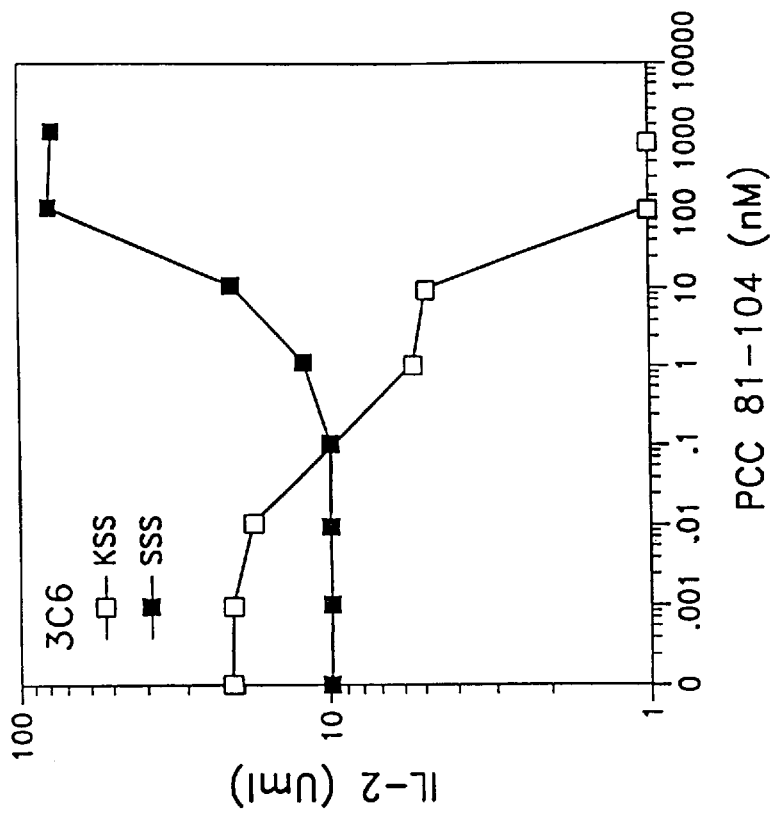
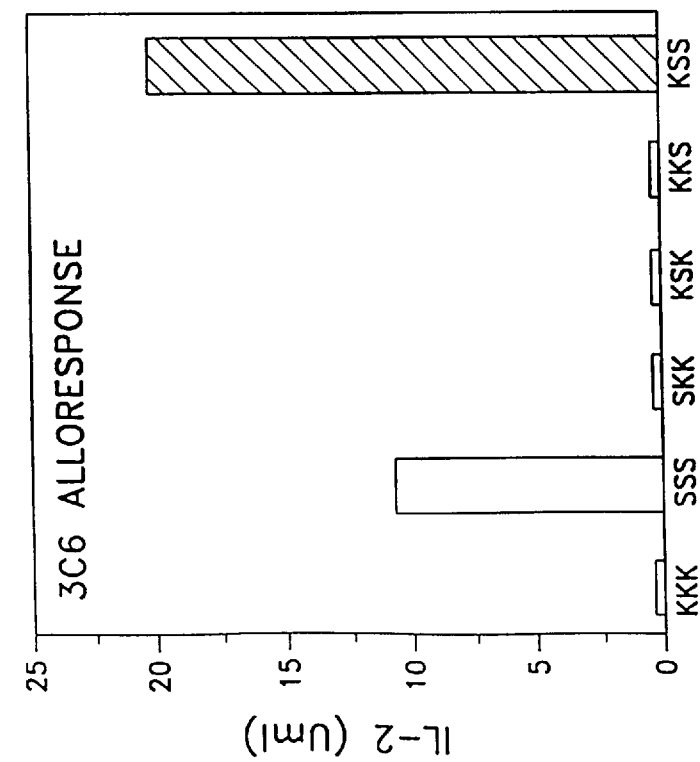
FIG. 1B
FIG. 1A

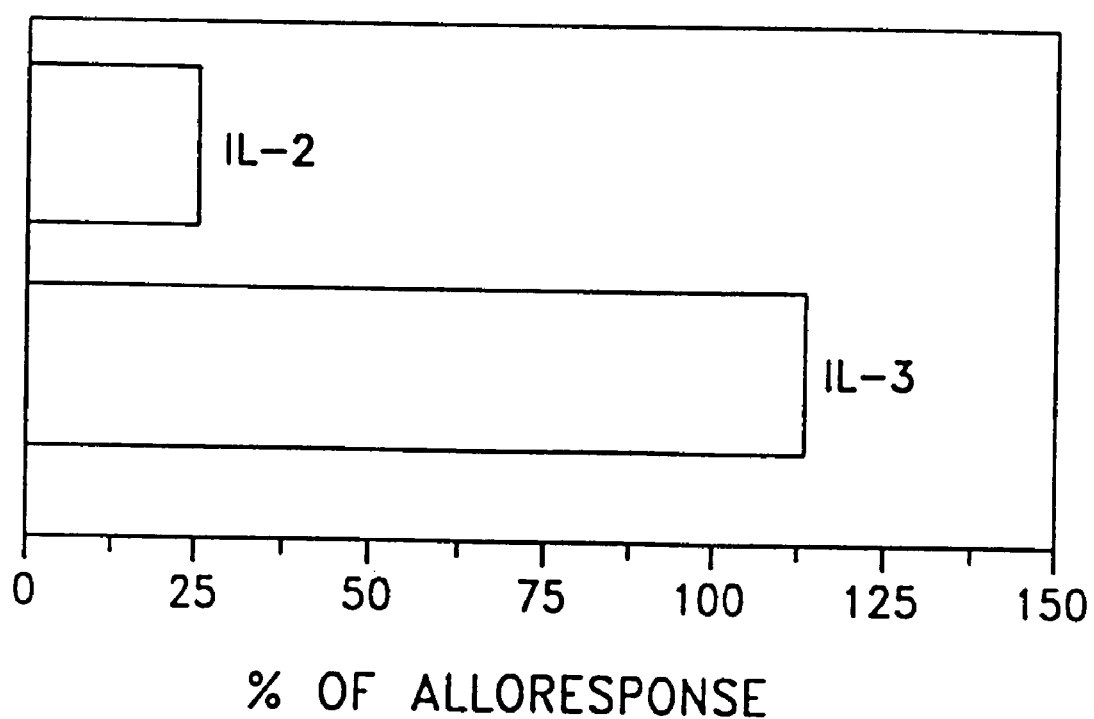

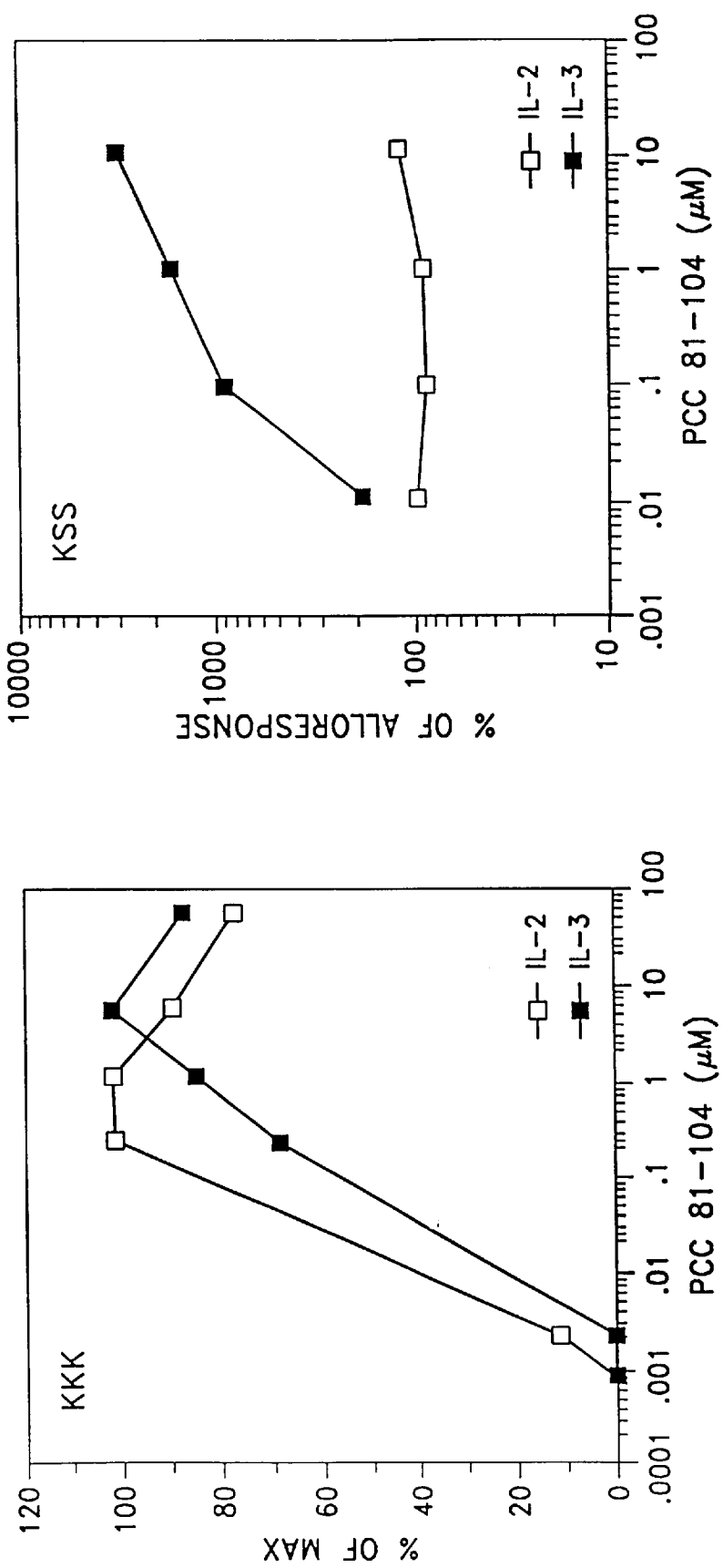

T CELL RECEPTOR LIGANDS AND METHODS OF USING SAME

This application is a divisional of U.S. patent application Ser. No. 08/004,936, filed Jan. 15, 1993, and now U.S. Pat. No. 5,837,477.

TECHNICAL FIELD OF THE INVENTION

The present invention concerns T cell receptor ligands, more particularly novel peptide-major histocompatibility complex class II molecule ligands, with novel immunomodulatory properties, as well as methods of using such ligands to modulate T cell effector responses, and methods to identify such ligands.

BACKGROUND OF THE INVENTION

Both humoral and cellular immune responses are essential components of defenses against pathogenic bacteria, viruses, and parasites. Key players in the immune response, called T lymphocytes, control cellular immunity by virtue of their ability to discriminate between a particular antigen and its close relative. This remarkable antigen specificity of the T lymphocyte responses is due to the presence on the T cell surface of clonally distributed, immunoglobulin-like T cell receptors (TCR) consisting of two non-identical glycosylated polypeptide chains, called $\alpha$ and $\beta$. T lymphocytes also express on their surface glycoproteins that are markers of different stages and types of T cell maturation (e.g., T3, T4, and T8 glycoproteins present on $CD3^+$, $CD4^+$ and $CD8^+$ T cells, respectively), which may mediate or augment specific T cell functions.

TCRs interact with antigens that have been processed by the antigen presenting cell (APC) to unfold or cleave the protein into peptide fragments, and are presented on the cell surface as part of a complex with a molecule encoded by genes within the major histocompatibility complex (MHC). $CD8^+$ and $CD4^+$ T lymphocytes interact with peptides bound to the polymorphic region of MHC class I or class II molecules, respectively (Townsend et al., Ann. Rev. Immunol., 7, 601–24 (1989); Rothbard et al., Ann. Rev. Immunol., 9, 527–65 (1991)). The TCR also interacts with proteins that have the capacity to generate intracellular second messenger signals that are essential to triggering T cell activation (Ashwell et al., Ann. Rev. Immunol., 8, 139–67 (1990)), or induction of T cell proliferation or differentiation. For example, recent data show that the CD3 $\gamma$, $\delta$, $\epsilon$: $\zeta/\eta$ complex stably associated with the TCR consists of at least two separate signal transduction modules that initiate second messenger cascades (Letourneur et al., Proc. Natl. Acad. Sci. USA, 88, 8905–09 (1991); Wegener et al., Cell, 68, 83–95 (1992)) which include primary events such as tyrosine phosphorylation (Samelson et al., Cell, 46, 1083–90 (1986)) and secondary events such as $PIP_2$ hydrolysis and elevation of $[Ca^{++}]_i$ (Weiss et al., Proc. Natl. Acad. Sci. USA, 81, 4169–73 (1984); June et al., J. Immunol., 144, 1591–99 (1990)).

The effect of these TCR-mediated biochemical events on the T cell is influenced by independent receptor-ligand interactions that may generate different types of signals from those evoked by the TCR-ligand interaction (Weaver et al., Proc. Natl. Acad. Sci. USA, 85, 8181–85 (1988); Mueller et al., J. Immunol., 144, 3701–09 (1990); Linsley et al., J. Exp. Med., 173, 721–30 (1991); Koulova et al., J. Exp. Med., 173, 759–62 (1991); Vandenberghe et al., J. Exp. Med., 175, 951–60 (1992)). Studies manipulating the potential of the APC to provide co-stimulation (Quill et al., J. Immunol., 138, 3704–12 (1987); Otten et al., Science, 251, 1228–31 (1991)) have separated effector activities of $CD4^+$ and $CD8^+$ T cells into activities that do (e.g., cytokine interleukin (IL)-2 production) and do not (e.g., cytokine IL-3 production and cell killing) require co-stimulatory signals.

The participation of co-stimulatory signals in control of production of IL-2 (Jenkins et al., Immunol. Rev., 95, 113–35 (1987)), the cytokine that is primarily responsible for clonal expansion following T cell activation, is indicated by the finding that metabolically-inactivated cells bearing ligands for the TCR present on $CD4^+$ cells are unable to effectively stimulate IL-2-dependent T cell proliferation (Bach et al., Immunol. Rev., 35, 76–96 (1977); Germain, J. Immunol., 127, 1964–66 (1981); Jenkins et al., J. Exp. Med., 165, 302–19 (1987)), which suggests there is a critical 'second signal' missing in these inactivated cells that operates independently of TCR-regulated second messenger generation or augmentation of TCR occupancy (Mueller et al., J. Immunol., 142, 2617–28 (1989a)). Several candidate receptor-ligand pairs have been suggested for the co-stimulatory pathway, such as the binding of B7 surface protein on the APC by CD28 on the responding T cell (Freeman et al., J. Exp. Med., 174, 625–31 (1991); Gimmi et al., Proc. Natl. Acad. Sci. USA, 88, 6575–79 (1991); Koulova et al., J. Exp. Med., 173, 759–62 (1991); Linsley et al., J. Exp. Med., 173, 721–30 (1991); Reiser et al., Proc. Natl. Acad. Sci. USA, 89, 271–75 (1992); Vandenberghe et al., J. Exp. Med., 175, 951–60 (1992)), and the recognition of the heat-stable antigen on the APC by an uncharacterized T cell counter-receptor (Kay et al., J. Immunol., 145, 1952–59 (1990); Liu et al., J. Exp. Med., 175, 437–45 (1992)).

Activation of the T cell is initiated when some adequate number of TCRs are aggregated at the interface between the T cell and the APC (Singer, Science, 255, 1671–77 (1992); Matis et al., Proc. Natl. Acad. Sci. USA, 80, 6019–23 (1983a); Ashwell et al., J. Immunol., 136, 757–68 (1986)). The extent of receptor-ligand aggregation depends on the number of available receptors on the T cell, the number of available ligands, i.e., peptide-MHC molecule complexes, on the APC, and the affinity of the TCR for the ligand. When a high level of peptide-MHC molecule complexes on the APC fails to induce T cell activation, it is believed this is due to a low affinity of the TCR for the ligand, which prevents receptor occupancy from exceeding the threshold needed for second messenger generation within the T cell (Fiering et al., Genes Dev., 4, 1823–34 (1990).

This affinity-based occupancy model predicts that in the presence of intact, metabolically-active APC capable of delivering co-stimulatory signals, peptide-MHC molecule complexes will be of two types: (1) agonists that can induce full T cell activation, and (2) non-agonists that do not induce T cell activation because of low affinity of the TCR for the peptide-MHC molecule complex, which prevents the number of occupied TCR from reaching the triggering threshold level (Matis et al., Proc. Natl. Acad. Sci. USA, 80, 6019–23 (1983a)). Recently, this model has been challenged by findings showing that substitution of a single residue in the peptide antigen for the TCR on a mouse Th2 clone prevented stimulation of proliferative responses, while permitting IL-4 cytokine production (Evavold et al., Science, 252, 1308–10 (1991)). This indicates that contrary to predictions of the affinity-based occupancy model, certain ligands can stimulate T cell second messenger generation without evoking the full repertoire of effector responses. Moreover, peptide analog-MHC molecule complexes have been described which inhibit the IL-2 response of the T cell response by TCR antagonism, or competition with wild-type ligand for binding to the TCR (De Magistris et al., *Cell*, 68, 625–34 (1992)). It has been reported that the inhibitory complexes were pure TCR antagonists which lacked capacity to generate intracellular signals (De Magistris et al., *Cell*, 68, 625–34 (1992)). This finding of an absence of second messenger generation despite fully occupied TCRs is also not predicted by the affinity based occupancy model.

The present invention is predicated on the unexpected discovery that there exist TCR ligands which exhibit selective antagonist properties (referred to herein as "selective antagonists") and which may also concurrently exhibit agonist properties (referred to herein as "mixed agonists-antagonists"). Specifically, peptide-MHC molecule complexes have been identified which interact with the TCR to actively and selectively inhibit IL-2 production by a mouse T cell clone, without preventing IL-3 production, IL-2Rα upregulation, or cell size enlargement induced by a TCR agonist. Since these new TCR ligands are able to selectively modulate certain T cell effector activities in a TCR-specific manner, they can be considered selective antagonists. These selective antagonists differ from the partial agonists described in Evavold et al., *Science*, 252, 1308–10 (1991), in that the selective antagonists of the present invention actively inhibit certain effector responses as opposed to simply failing to stimulate these responses. These selective antagonists differ from the complete antagonists described in De Magistris et al., *Cell*, 68, 625–34 (1992), in that unlike the complete antagonists, the selective antagonists of the present invention have been shown to selectively inhibit certain effector responses, without affecting others, and act without preventing all T cell signaling.

These results suggest there may be two distinct classes of inhibitory peptide-MHC molecule complexes: selective antagonists and complete antagonists. While members of the latter class would prevent intracellular messenger generation in the T cell by removing TCRs from the functional pool and precluding any effector responses, members of the former class would interfere with certain effector activities based on qualitative differences in requirements for intracellular signalling, possibly, but not necessarily, related to the co-stimulation dependence of the analyzed functions.

The properties of the TCR ligands of the present invention have important implications for models of thymic selection and peripheral T cell activation and provide new pharmacological approaches to the treatment of autoimmune disease, to the problems of graft rejection, and in vaccine design. Moreover, the present invention described herein enables the identification, characterization, development, and utilization of the TCR ligands of the present invention.

Consequently, it is an object of the present invention to provide a TCR ligand which inhibits at least one T cell effector response evoked by fully active peptide-MHC molecule complexes available to responding T cells, without necessarily inhibiting all other effector responses of the T cells. It is a related object of the present invention to provide a TCR ligand which inhibits at least one T cell effector response evoked by fully active peptide-MHC molecule complexes available to responding T cells and which does not substantially inhibit at least one other T cell effector response. It is another object of the present invention to provide a TCR ligand which inhibits co-stimulation dependent T cell effector responses evoked by fully active peptide-MHC molecule complexes available to responding T cells and which does not block co-stimulation independent T cell effector responses under the same conditions. It is yet another object of the present invention to provide TCR ligands which are selective antagonists and mixed agonists-antagonists. It is a further object of the present invention to provide a method of identifying, as well as preparing, such TCR ligands and of providing improved methods of modulating T cell effector response utilizing such TCR ligands.

These and other objects and advantages of the present invention, as well as additional inventive features, will be apparent from the description of the invention provided herein.

BRIEF SUMMARY OF THE INVENTION

The present invention provides a TCR ligand which substantially inhibits at least one T cell effector response evoked by fully active peptide-MHC molecule complexes available to responding T cells without necessarily substantially inhibiting, and preferably not substantially inhibiting, at least one other T cell effector response evoked by fully active peptide-MHC molecule complexes available to responding T cells. The present invention further provides for a TCR ligand which inhibits co-stimulation dependent T cell effector responses evoked by fully active peptide-MHC molecule complexes available to responding T cells and which does not block co-stimulation independent T cell effector responses under the same conditions. The present invention provides TCR ligands which are selective antagonists and mixed agonists-antagonists.

The present invention additionally provides methods of using such TCR ligands to modulate T cell effector responses, as well as methods to identify, and develop candidate members of, such TCR ligands.

BRIEF DESCRIPTION OF THE DRAWINGS

FIG. 1 sets forth the response of 3C6 Th1 cells to pigeon cytochrome C (PCC) peptide PCC 81-104 presented by EαEβ$^k$ molecules with different mutations in the βHV3 region as measured by stimulation of IL-2 production. FIG. 1A demonstrates alloreactivity of 3C6 Th1 cells to the mutated EαEβ$^k$ molecules in the absence of peptide. FIG. 1B demonstrates the response of 3C6 Th1 cells to MHC EαEβ molecules with β72$^s$, 75$^s$, 79$^s$ (sss) or β75$^s$, 79$^s$ (kss) mutant chains in the presence of PCC 81-104 peptide.

FIG. 2 sets forth the inhibitory effect of different peptides on alloreactive stimulation of IL-2 production in 3C6 Th1 cells by MHC molecules with kss Eβ chains and shows that the inhibitory effect is related to peptide ability to be recognized by the 3C6 receptor.

FIG. 3 sets forth the ability of a peptide to bind MHC molecules with kss Eβ chains and shows that this binding ability does not correlate with its ability to inhibit alloreactive stimulation of IL-2 production in 3C6 Th1 cells.

FIG. 4 sets forth the inhibitory effect of PCC 81-104 and shows that high dose inhibition does not account for the inhibitory effect of PCC 81-104 on alloreactive stimulation of IL-2 production in 3C6 Th1 cells by L cells expressing MHC molecules with kss Eβ chains.

FIG. 5 sets forth the inhibitory effect of PCC 81-104 and shows that the PCC 81-104 peptide-mediated inhibition of alloreactive stimulation of IL-2 production in 3C6 Th1 cells is selective and does not prevent other TCR-dependent activation events. FIGS. 5C and 5D demonstrate reverse transcription-PCR analysis of RNA extracted from co-cultures of 3C6 Th1 cells and transfected L cells expressing MHC molecules with kss Eβ chains in the absence or presence of PCC 81-104 (1 μM). While FIG. 5C shows ethidium staining of PCR products, FIG. 5D shows shows the calculated relative amounts of IL-2 and IL-3 mRNA.

FIG. 7 sets forth the inhibitory effect of PCC 81-104 and shows that PCC 81-104 does not inhibit the stimulation of IL-2 production and can increase the stimulation of IL-3 production in C6E1 hybridoma cells by L cell transfectants expressing MHC molecules with kss Eβ chains. FIG. 7A demonstrates the response of the C6E1 hybridoma cells to PCC 81-104 peptide presented by L cells expressing MHC molecules with wild-type kkk Eβ chains and measured by stimulation of production of IL-2 and IL-3. Data are expressed as percent of maximal stimulation for IL-2 and for IL-3. FIG. 7B demonstrates the response of the C6E1 hybridoma cells to PCC 81-104 peptide presented by L cells expressing MHC molecules with kss Eβ chains and measured by stimulation of production of IL-2 and IL-3. Data are expressed as percent of the response obtained in the absence of PCC 81-104 peptide.

FIG. 8 sets forth the inhibitory effect of PCC 81-104 and shows that antibody cross-linking of CD28 on 3C6 Th1 cells does not prevent selective PCC 81-104 peptidemediated inhibition of alloantigen stimulated production of IL-2.

DESCRIPTION OF THE PREFERRED EMBODIMENTS

Figure 2A:
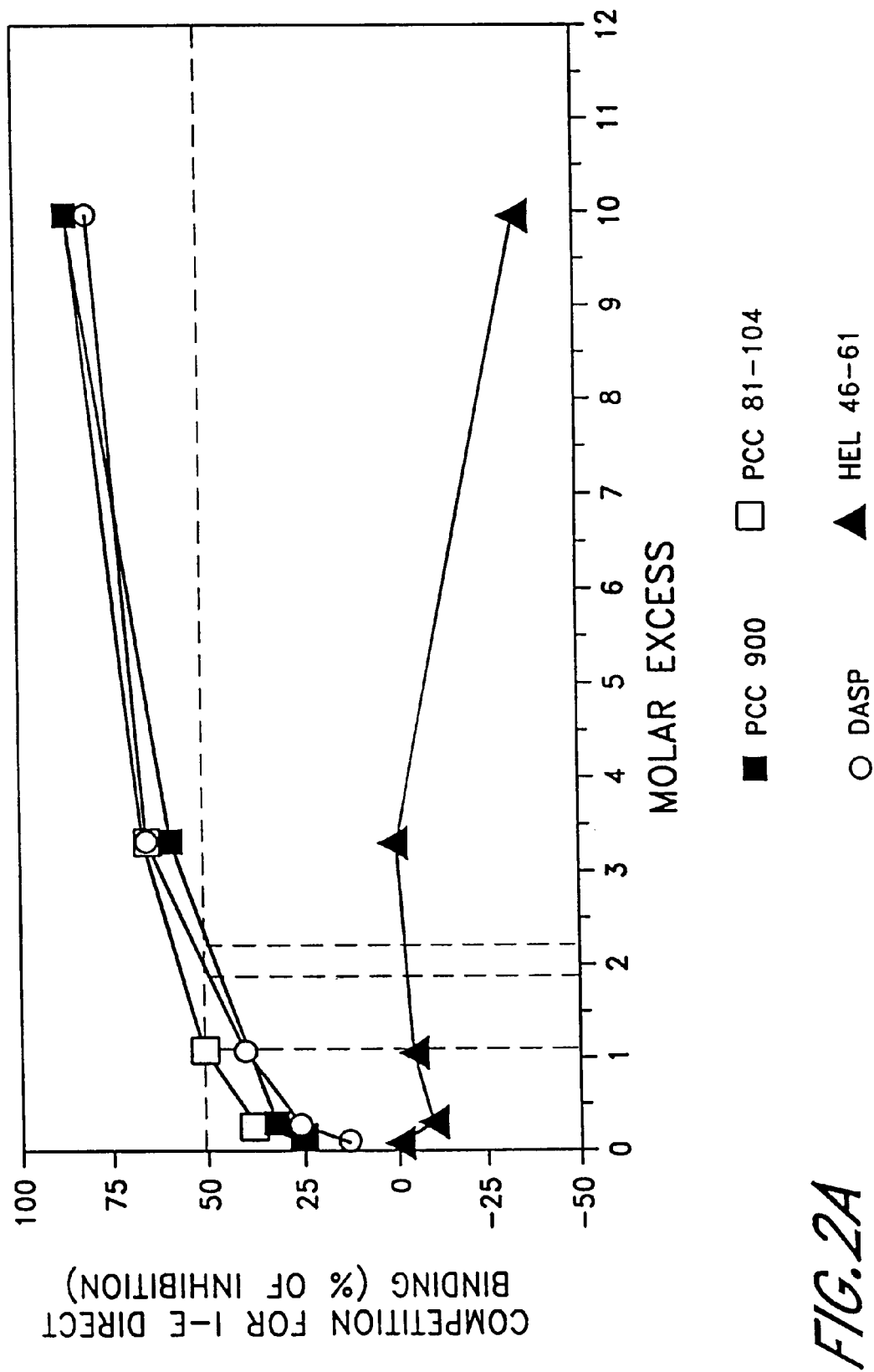
FIG. 2A demonstrates binding of the peptides PCC 81-104, PCC 81-104 [99Q], DASP, and HEL 46-61 to transfected L cells expressing MHC molecules with kss Eβ chains as measured by competition for binding of biotinylated-DASP (25 μM). Data are expressed as percent inhibition at each competitor concentration.

The present invention concerns TCR ligands with immunomodulatory properties. Specifically, the present invention provides TCR ligands capable of interfering with the elicitation of T cell effector responses. Ligands comprised of mutated MHC class II molecules verified that a single alteration in the structure of the TCR ligand on physiologically intact APC can inhibit at least one T cell effector response evoked by fully active peptide-MHC molecule complexes available to responding T cells. The present findings also reveal a remarkable and previously undisclosed class of peptide-MHC molecule complexes which, unlike the previously described complete antagonists, have been shown to substantially inhibit at least one T cell effector response (e.g., stimulated production of IL-2) without substantially inhibiting other T cell effector responses (e.g., induction of IL-3 secretion, IL2Rα up-regulation, and size-enlargement responses).

The present invention provides new classes of TCR ligands called selective antagonists and mixed agonists-antagonists. The selective antagonists and mixed agonists-antagonists differ from the previously described partial agonists in that, rather than merely failing to stimulate certain effector responses, these new TCR ligands can actively inhibit effector responses (e.g., stimulated IL-2 production) that would otherwise be evoked by agonist ligands on the same APC.

The selective antagonist of the present invention is a TCR ligand which substantially inhibits at least one T cell effector response evoked by fully active peptide-MHC molecule complexes available to responding T cells and preferably, but not necessarily, does not substantially inhibit at least one other T cell effector response evoked by fully active peptide-MHC molecule complexes available to responding T cells (i.e., that particular T cell or a T cell population).

The mixed agonist-antagonist of the present invention is a TCR ligand which substantially inhibits at least one T cell effector response evoked by fully active peptide-MHC molecule complexes when made available to responding T cells and which, while inhibiting one or more T cell effector responses, stimulates one or more different T cell effector responses. The mixed agonist-antagonist preferably, but not necessarily, does not substantially inhibit at least one other T cell effector response evoked by fully active peptide-MHC molecule complexes when made available to responding T cells.

Both the selective antagonist and the mixed agonist-antagonist may also, and preferably do, inhibit costimulation dependent T cell effector responses evoked by fully active peptide-MHC molecule complexes available to responding T cells and without blocking co-stimulation independent T cell effector responses under the same conditions. Several observations described herein, such as the selective inhibitory effect of peptide ligand on IL-2 production, the dramatic effect of fixation of APC on the IL-2 but not IL-3 antigen dose-response relationship, and the failure of peptide ligand to inhibit IL-2 production by a T cell hybridoma, confirm that the peptide-mutant MHC molecule complexes can inhibit co-stimulation dependent T cell effector responses evoked by fully active peptide-MHC molecule complexes by interfering with the production of, or response to, co-stimulatory signals.

Moreover, soluble antibody directed against CD28 affected the 3C6 response to alloantigen in a manner similar to addition of PCC peptide, in that IL-3 responses were maintained in the face of inhibition of IL-2 production. Antibody-mediated cross-linking of CD28 on 3C6 Th1 cells abrogated the inhibition of alloresponses by soluble CD28 and slightly increased the IL-3 response. This verifies effective stimulation of the CD28 pathway. However, cross-linking of the CD28 molecules did not prevent the inhibition of IL-2 production mediated by PCC-mutant MHC class II molecule complexes. These observations suggest that an interaction between B7 and CD28 may be necessary but not sufficient for observation of the IL-2 alloresponse. Alternatively, it is also possible that the intracellular signals delivered through CD28 are not effective when the 3C6 TCR is engaged with the PCC peptide-mutant E$\alpha$E$\beta$ complexes, which would suggest generation of dominant-negative intracellular messengers by the incomplete agonists. Irrespective of whether the site of defective signalling is the T cell or the APC, the ability of relatively small numbers of ligands in accordance with the present invention to interfere with T cell effector responses in the presence of complete agonist ligand implies that introduction of ineffective TCR-ligand complexes into the signalling assemblies at the T cell-APC interface interferes in a nonlinear way with signal generation.

In addition to providing novel TCR ligands, the present invention provides for a method of identifying such TCR ligands. The identification method for the selective antagonists comprises contacting T cells with an agonist capable of effecting known T cell effector responses and a candidate TCR ligand and determining whether the candidate TCR ligand substantially inhibits at least one T cell effector response. The present inventive method preferably further comprises determining whether the candidate TCR ligand substantially inhibits at least one T cell effector response while not substantially inhibiting at least one other T cell effector response. In carrying out the identification method, the T cells may be contacted with the agonist and candidate TCR ligand in any suitable manner. Preferably, the T cells are simultaneously contacted with the agonist and the candidate TCR ligand by contacting the T cells with a mixture of the agonist and the candidate TCR ligand. While the mixture of the agonist and the candidate TCR ligand may be formed in any suitable manner, the mixture of agonist and candidate TCR ligand is preferably formed by contacting MHC molecules with a first peptide to form the agonist and then with a second peptide to form the candidate TCR ligand. Alternatively, the T cells are contacted with the agonist and then the T cells and the agonist are contacted with the candidate TCR ligand.

The identification method for the mixed agonists-antagonists is the same as that for selective antagonists with the additional step of separately contacting T cells with a candidate TCR ligand, with and without an agonist capable of effecting known T cell effector responses, and evaluating T cell effector responses to the candidate TCR ligand alone as well as comparing the inhibitory effect of the candidate TCR ligand on at least one of the known T cell effector responses to agonists.

The present invention not only comprises methods of identifying the TCR ligands of the present invention, but also contemplates methods of preparing candidate TCR ligands of the present invention. The method of preparing candidate TCR ligands as possible selective antagonists or mixed agonists-antagonists of the present invention comprises identifying a peptide which binds to MHC molecules to form a complex which can evoke a T cell effector response, determining which residues of the peptide can be substituted so as not to affect binding to the MHC molecules, determining which of the non-binding-effect residues of the peptide affect recognition of the peptide-MHC molecule complexes by T cells, substituting the non-binding-effect/recognition-effect residues of the peptide to form substituted peptides, and screening the substituted peptides to identify those substituted peptides which have less agonistic effect or a distinct spectrum of agonist effects (e.g., with respect to different agonist effects) as compared to the unsubstituted peptides as candidate TCR ligands. The substituted peptide-MHC molecule ligands can then be further screened by contacting T cells with an agonist capable of effecting known T cell effector responses and one of the candidate TCR ligands and determining whether the candidate TCR ligand substantially inhibits at least one T cell effector response or, preferably, whether the candidate TCR ligand substantially inhibits at least one T cell effector response while not substantially inhibiting at least one other T cell effector response.

While the present inventive methods of preparing candidate TCR ligands, and identifying those TCR ligands of the present invention, have applicability in developing TCR ligands useful in managing autoimmune diseases and problems of graft rejection, these present inventive methods also have applicability in vaccine design, especially in cases in which some components of an immune response have pathological rather than beneficial effects. In particular, selective antagonists can be designed with the capacity to selectively guide the immune response along certain pathways and avoid vaccine-induced immune responses that cause pathology. For example, the split in cytokine production seen with such selective antagonists can also be used to deviate immune responses following vaccination away from those that sometime potentiate disease upon subsequent infection and towards those that are highly protective.

The present invention also comprises a method of using the T cell ligands described herein to modulate T cell effector responses by contacting T cells with the TCR ligands of the present invention. More particularly, the present invention includes a method of modulating the immune response of a host by administering to the host the TCR ligands of the present invention.

The ability of the presently described TCR ligands to dominantly interfere with T cell effector function has implications for the creation of new approaches to autoimmune disease treatment, problems of graft rejection, and vaccine design.

The presently described ligands able to engage TCRs and deviate the response of T lymphocytes to simultaneously available agonist ligands for the same TCR can be employed as highly selective agents to interrupt the effector activities of autoimmune T cells responding to self-antigen-MHC molecule complexes or alloimmune T cells responding to tissue graft antigens. Previous approaches to the interruption of autoimmune disease processes or graft rejection caused by T cell activity have involved use of general immunosuppressive agents such as steroids or cyclosporin A/FK506, cytotoxic agents such as cyclophosphamide or methotrexate, and peptides that can physically block the MHC molecule binding site and prevent presentation of the peptides involved in the disease or rejection process. These methods are fraught with numerous problems. For example, general immunosuppressives or non-selective cytotoxic agents leave the patient more prone to infection and to development of malignancies, and are associated with a high level of undesirable side-effects, such as renal and liver damage. Similarly, blocking the MHC binding site requires massive amounts of material to achieve the necessary quantitative blocking effect, may be accompanied by induction of undesirable strong immune responses to the blocking agent itself, and calls for continuous treatment since the effect on the T cells is not prolonged. Moreover, the evidence does not support that peptides which block the MHC binding site can affect presentation of self-antigens that are pre-associated with MHC molecules, which would be necessary for treatment when active disease is already present, or with allogeneic grafts.

The complete antagonists described in De Magistris et al., *Cell*, 68, 625–34 (1992), avoid several of these problems as the antagonists are immunologically specific and thus affect only a small subset of T cells relevant to disease. This reduces chances of adverse systemic or organ-specific side-effects, and lessens the amount of material necessary for administration as compared to the MHC molecule blocking strategy. However, these complete antagonists employed have been claimed not to generate intracellular signals (De Magistris et al., *Cell*, 68, 625–34 (1992)), which means that any effects of administration would be transient. In distinct contrast, the present inventive approach is specific and also may allow longer-lasting inactivation of autoimmune T cells, as the novel TCR ligands described herein appear to require intracellular second messenger generation and selectively inhibit only a subset of the responses of the T cell. Additionally, administration of the novel TCR ligands of the present invention could potentially drive autoimmune T cells into a long-term unresponsive state. This is because T cell signalling in the absence of co-stimulation frequently leads to a state of unresponsiveness termed anergy (Schwartz, *Science*, 248, 1349–56 (1990)). Therefore, a selective antagonist or mixed agonist-antagonist in accordance with the present invention may potentially be able to block ongoing autoimmune T effector activity, as might a complete MHC blocking peptide, and administration of such a TCR ligand may lead to a lasting decrease in autoimmune disease due to anergy induction among the self-reactive T cells. In this fashion, ligand administration could diminish or slow the progression of the autoimmune disease process, or lengthen the survival of grafts. This would be accomplished with few or no side-effects, due to the extreme specificity of the drug for only the disease-causing or graft-rejecting T cells.

Both in vitro and in vivo applications are contemplated in the context of the present invention. It will be recognized that for the different applications, the TCR ligand may be employed in any suitable form and may be formed in situ. Thus, the present invention contemplates the formation of a suitable TCR ligand through use of a suitable peptide, MHC molecule, or peptide-MHC molecule complex, which may be used alone or in appropriate association with other agents, and which may be introduced by addition to cells, expression in cells, presentation on the surface of APC, or introduction by any other appropriate means or combination of means. The TCR ligand or ligand component may be present in a pharmaceutical composition in any suitable quantity. The pharmaceutically acceptable excipients described herein, for example, vehicles, adjuvants, carriers, or diluents, are readily available to the public.

As regards these applications, the present inventive method includes the administration to an animal, particularly a human, of a therapeutically effective amount of one or more of the aforementioned TCR ligands or ligand components as an active agent effective in the treatment of any condition involving the desirability of modulating T cell effector responses, particularly autoimmune disease and problems of graft-host rejection. One skilled in the art will appreciate that suitable methods of administering a compound of the present invention to an animal are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. However, pharmaceutically acceptable excipients which do not interfere with the desired effect on the T cell effector response are, of course, preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freezedried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the TCR ligands or ligand components employed in the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention should be sufficient to effect a prophylactic or therapeutic response in the animal over a reasonable time frame. One skilled in the art will recognize that dosage will depend upon a variety of factors including the strength of the particular compound employed, the condition of the animal, the body weight of the animal, as well as the severity of the adverse condition or infection and stage of the condition or disease. The size of the dose will also be determined by the existence, nature, and extent of any adverse side-effects that might accompany the administration of a particular compound. Suitable doses and dosage regimens can be determined by comparisons to agents presently used in the treatment of autoimmune disease and problems of graft-host rejection. The preferred dosage is the amount which results in the desired effect on T cell effector response, without significant side effects. In proper doses and with suitable administration of certain compounds, the present invention provides for a wide range of alteration of T cell effector responses, e.g., from little alteration to essentially either complete induction or inhibition.

The following examples further illustrate the present invention but, of course, should not be construed as in any way limiting its scope.

EXAMPLES

The following experimental procedures were employed in carrying out the experiments which form the examples described herein.

cDNA Constructs and L Cell Transfectants cDNA expression constructs encoding wild-type $E\beta^K$ (kkk) and mutant chains including $\beta75^s$, $79^s$ (kss), $\beta72^s$, $75^s$, $79^s$ (sss), $\beta72^s$ (skk), $\beta75^s$ (ksk) and $\beta79^s$ (kks) were created as described in Racioppi et al., *J. Immunol.*, 147, 3718–27 (1991). These plasmids were co-transfected into the DAP.3 subline of mouse L cells (Margulies et al., *J. Immunol.*, 130, 463–70 (1983)) together with a construct encoding wild-type $E\alpha$ and a plasmid containing a marker gene for drug selection. Drug-resistant clones expressing suitable surface levels of $E\alpha E\beta$ dimers were isolated as described in Racioppi et al., *J. Immunol.*, 147, 3718-27 (1991).

Peptides

The CNBr fragment 81-104 from pigeon cytochrome c (PCC 81-104) was prepared as described in Corradin et al., *Biochim. Biophys. Acta.*, 221, 489–496 (1970). DASP, an analogue of moth cytochrome c (residues 86–90 linked to residues 94-103), as well as PCC 88-104, hen egg lysozyme (HEL) 81-96, and HEL 46-61 with or without an $NH_2$-terminal long-chain biotin (Busch et al., *Int. Immunol.*, 2, 443–51 (1990)) were synthesized and purified by Dr. John Coligan, Biological Resources Branch, NIAID, NIH, Bethesda, Md. DASP conjugated to an $NH_2$-terminal long-chain biotin was prepared and kindly donated by Dr. Jonathan Rothbard, ImmuLogic Corp., Palo Alto, Calif. PCC 81-104 [99Q] was the kind gift of Dr. Ronald Schwartz, LCMI, NIAID, NIH, Bethesda, Md.

T Cell Clones and Hybridomas

The 3C6 T cell clone was produced as described in Matis et al., *J. Immunol.*, 130, 1527–35 (1983b) from pigeon cytochrome c-immune spleen cells of a B10.A mouse. The C6E1 T cell hybridoma was produced from the 3C6 clone by fusion to BW1100 (White et al., *J. Immunol.*, 143, 1822–5 (1989)), which lacks its own functionally rearranged TCR a and β gene loci. The hybridoma and the T cell clone were grown in RPMI-1640 medium with 10% fetal calf serum (FCS), 2 mM glutamine, and nonessential amino acids. The 3C6 cytochrome c-specific T cell clone was maintained in vitro by stimulation with antigen and irradiated spleen cells, followed by a period of rest in the absence of antigen. Cells collected at end of the resting phase were centrifuged over a Ficoll gradient and treated with a cocktail of I-A specific and I-E specific mAbs. Antibody-treated T cells were negatively selected by sorting with magnetic beads (DYNAL, Norway) and an MPC-1 magnetic concentrator as recommended by the supplier.

T Cell Functional Assays

Production of IL-2 and IL-3 in response to L cell transfectants in the presence or absence of added peptide was measured as described in Ronchese et al., *Nature*, 329, 254–6 (1987b). In brief, $2-5\times10^4$ T cells were incubated with $2-5\times10^4$ transfected L cells in the wells of 96-well flat bottom culture plates in 200 μl of complete medium with or without various concentrations of peptide antigen. Supernatants were collected after 24 hours and assayed for IL-2 content using CTLL indicator cells, or for IL-3 content using FDC.1 cells. IL-2 and IL-3 units were calculated as the inverse of the dilution giving 50% of the maximum $^3$H-thymidine incorporation by CTLL (IL-2) or FDC.1 (IL-3) cells observed with reference IL-2 and IL-3 preparations. Proliferative responses were measured by assessing $^3$H-thymidine incorporation between 48–66 hrs of culture. For experiments in which the data are expressed as "% max" or "% alloresponse", the actual absolute 100% responses were: IL-2 alloresponse, 10–40 units/ml; IL-3 alloresponse, 100–500 units/ml; IL-2 response to $E\alpha E\beta^k$ plus PCC peptide, 150–300 units/ml; IL-3 response to $E\alpha E\beta^k$ plus PCC peptide, 1000–10,000 units/ml; IL-2 response to fixed cells bearing $E\alpha E\beta^k$ plus PCC peptide, 30–50 units/ml; IL-3 response to fixed cells bearing $E\alpha E\beta^k$ plus PCC peptide, 50–200 units/ml.

For analysis of the effects of mAb directed against CD28 on the response of the 3C6 Th1 clone, $5\times10^4$ 3C6 Th1 cells were co-cultured with $5\times10^4$ transfected L cells expressing the allostimulatory MHC molecule with kss chains in the presence or absence of varying dilutions (1:250–1:16,000)

of ascites containing hamster anti-mouse CD28 mAb (Harding et al., Nature, 356, 607–9 (1992)). IL-2 and IL-3 accumulation in these cultures was measured as described above. Where indicated, CD28 was cross-linked on the cell surface by first pre-incubating the 3C6 Th1 cells with the mAb for 1 hour at 4° C., washing the cells, and then adding polyclonal anti-hamster IgG antisera (Caltag) to a final dilution of 1:40. Following incubation for 1 hour at 4° C., the cells were washed before use in a standard stimulation culture.

Flow Cytometric Analysis

Analysis of cell-surface class II MHC molecule expression by transfected cells was carried out using the anti-Eα mAb 14.4.4S (Ozato et al., J. Immunol., 124, 533–40 (1980)) and FITC-goat anti-mouse F(ab)'2 as the detection reagent (Ronchese et al., J. Immunol., 139, 629–38 (1987a)). Cells were analyzed using either an EPICS V, FACSAnalyzer, or FACScan. For multiparameter analysis of 3C6 Th1 cells incubated with APC with or without peptide, 3C6 Th1 cells (0.5×10$^5$) were co-cultured with FT 27.2.A2 I-E expressing L cells (0.5×10$^5$) that had been preincubated for 1 hour at 37° C. with PCC 81-104 peptide (20 μM). After 24 hour of incubation, cells recovered from the 48 well plate were stained using an anti-Thy 1.2 mAb labeled with FITC (Becton-Dickinson) and mAb 7D4, an anti IL2-Rα specific reagent (Malek et al., Proc. Natl. Acad. Sci. USA, 80, 5694–8 (1983)). Detection of bound 7D4 was with R-PE labelled goat anti-rat antibody (Caltag). Cells were analyzed on a FAScan flow cytometer. Cells were gated on Thy 1.2 staining, and the positive cells (i.e., 3C6 Th1 cells) were analyzed for 7D4 expression and cell size (SSC [side-scatter] parameter). Supernatants of these cultures were assayed for IL-2 and IL-3 content. Parallel cultures were analyzed for $^3$H-thymidine incorporation.

Measurement of Peptide Binding Using Biotinylated Peptides

A modified version of the assay described in Busch et al., Int. Immunol., 2, 443–51 (1990), was used to measure peptide binding to cell-associated class II MHC molecules. After extensive washing in phosphate buffered saline (PBS)-1% bovine serum albumin (BSA), 2×10$^5$ DAP.3 cells or DAP.3 transfectants expressing various EαEβ molecules were incubated at 37° C. in 200 μl of PBS-2% FCS containing the indicated concentration of biotinylated peptide. In the competition experiments competitors were added at the same time as labeled peptide and at the indicated concentrations. After 4 hours, the cells were washed and stained with a sandwich of FITC-avidin (Vector), biotinylated-anti-avidin (Vector), and FITC-avidin (Vector). After washing, the cells were analyzed on a FAScan flow cytometer for fluorescence. Only viable cells were considered in the analysis, as determined by PI staining. The data are expressed as net mean fluorescence intensity (MFI), calculated by subtracting from the actual MFI the MFI obtained by staining in the absence of biotinylated-peptide. Percent inhibition in the competition experiments was calculated as: % of I=(net MFI without competitor—net MFI with competitor)/(net MFI without competitor×100%).

Measurement of Cytokine mRNA Levels

3C6 Th1 cells were co-cultured with FT 27.2.A2 cells expressing the allostimulatory mutant EαEβ class II molecule that had previously been incubated with PCC 81-104 peptide for 1 hour at 37° C. After 4 hours of co-culture, total RNA was extracted by the guanidinium thiocyanate phenol-chloroform method (Chomczynski et al., Anal. Biochem., 162, 156–9 (1987)), quantified spectro-photometrically, and analyzed on a denaturing agarose gel. Reverse transcription of 1 μg of total RNA with 37.5 μg/ml of an oligo d(T)$_{12-18}$ (Collaborative Research) was performed for 1 hour at 42° C. using 600 U of M-MLV reverse transcriptase (GIBCO BRL) in 50 mM Tris-HCl, pH 8.3, 3 mM MgCl$_2$, 60 mM KCl, 10 mM dithiothreitol, 75 μg/ml of acetylated BSA, 1 unit/ml of RNasin (Promega) and 1 mM of each of dATP, dGTP, dCTP, dTTP. 1 μCi of $^{32}$P-dCTP (3000 μCi/mM, Amersham) was added to the reaction mixture. The efficiency of the reverse transcription reaction was assayed by comparing the TCA-precipitable radiolabeled cDNA present in each sample. PCR analysis was performed on cDNA samples adjusted to contain the same amounts of TCA-precipitable labeled material. One-tenth of the product cDNA was combined with 1 μM of each of the specific IL-2 and IL-3 primers (Cytokine Mapping Amplimers™, Clontech), 200 μM of each dNTP, and 1.25 U of Taq DNA polymerase (5 U/ml, Perkin Cetus) in 1× PCR buffer (10 mM Tris-HCl, pH 8.3, 50 mM KCl, 2.5 mM MgCl$_2$, 100 μg/ml BSA). Total volume was 50 μl. PCR reactions were performed as described in the Cytokine Mapping Amplimerst™ manual (Clontech). The number of cycles was adjusted to fall in the log linear range of signal for these amplimers and cDNA source. PCR products were analyzed on 5% polyacrylamide pre-cast TBE gels (Bio-Rad). Gels were dried and radiolabeled bands were quantified using a Phosphor-Imager (Molecular Dynamics). Images were analyzed by Image Quant™ version 3.15 software (Molecular Dynamics).

Example 1

This example sets forth a mutant peptide-MHC class II molecule complex that is a TCR ligand in accordance with the present invention and illustrates peptide inhibition of alloreactive stimulation of IL-2 production in a T cell clone by the TCR ligand.

3C6 is a Th1-type (Mosmann et al., J. Immunol., 136, 2348–57 (1986)) cloned cell line derived from a pigeon cytochrome c (PCC)-immunized B10.A mouse that increases its production of IL-2 when stimulated by splenic APC as well as C-terminal PCC peptides including the CNBr fragment 81-104 (PCC 81-104). In addition to the expected specific activation of 3C6 Th1 cells by PCC peptides presented by cells expressing the wild-type EαEβ$^k$ MHC class II molecule, 3C6 Th1 cells also respond alloantigenically to APC expressing the closely related EαEβ$^s$ molecule. This alloantigenic response can be obtained in the absence of added antigen, which has been observed for other cytochrome c-reactive T cells (Matis et al., J. Immunol., 130, 1527–35 (1983b)), as well as for other alloresponses.

Transfected mouse L cells expressing MHC class II molecules with mutant Eβ$^k$ proteins containing various Eβ$^s$ allelic substitutions were produced to examine the relationships among MHC molecule structure, peptide antigen presentation, and allorecognition (Racioppi et al., J. Immunol., 147, 3718–27 (1991)). Transfectants were examined that expressed EαEβ MHC molecules with wild-type Eβ chains (kkk), and Eβ chains containing substitutions of E$^s$ allelic residues at positions 75 and 79 (kss), at positions 72, 75, and 79 (sss), at position 72 (skk), at position 75 (ksk), and at position 79 (kks) in the putative helix of the peptide-binding region.

While tranfectants expressing MHC molecules with wild-type (kkk) chains, or chains possessing a single allelic substitution (skk, ksk, kks) failed to evoke stimulation of IL-2 synthesis in 3C6 Th1 cells in the absence of peptide, transfectants expressing MHC molecules with chains possessing multiple allelic substitutions (sss, kss) evoked a substantial peptide-independent, alloantigenic response (FIG. 1A).

3C6 Th1 was then tested for its response to PCC 81-104 peptide presented on the APC in association with the two types of MHC molecules with mutant Eβ chains (i.e., sss and kss) capable of mediating alloreactive stimulation of IL-2 production. In addition to inducing a peptide-independent alloresponse, a clear dose-dependent stimulation of IL-2 production by PCC 81-104 peptide was observed with APC expressing MHC molecules with sss chains (FIG. 1B). Unexpectedly, addition of the same peptide to cells expressing MHC molecules with kss chains not only failed to stimulate IL-2 production above that seen in the absence of peptide, but decreased IL-2 levels with increasing peptide doses to levels below those observed in the alloantigenic response (FIG. 1B).

Example 2

This example confirms that the PCC peptide-mediated inhibition of alloreactive stimulation of IL-2 production in 3C6 Th1 cells demonstrated in Example 1 cannot be explained by competition with other peptides for binding with MHC molecules possessing kss chains.

Substantial evidence supports that many T cell responses to alloantigenic MHC molecules involve recognition of the peptide(s) bound to the non-self MHC molecules (Heath et al., *Nature*, 341, 749–52 (1989); Lombardi et al., *J. Immunol.*, 142, 753–9 (1989); Cotner et al., *J. Immunol.*, 146, 414–7 (1991); Rotzschke et al., *J. Exp. Med.*, 174, 1059–71 (1991)). Thus, one explanation for the ability of the PCC 81-104 peptide to inhibit the 3C6 Th1 alloresponse to the mutant MHC class II molecule with kss chains would be that it competes for MHC binding with another peptide that is necessary for the formation of the alloantigenic ligand recognized by the 3C6 Th1 receptor. Competition at the level of the MHC molecule has been suggested as an explanation for previous observations of exogenous peptide inhibition of allogeneic stimulation (Rock et al., *J. Exp. Med.*, 159, 1238–52 (1984); Eckels et al., *Proc. Natl. Acad. Sci. USA*, 85, 8191–5 (1988); Wei et al., *J. Exp. Med.*, 174, 945–8 (1991)). However, it is usually difficult to block MHC-dependent responses by adding a competing peptide after the stimulatory peptide has had an opportunity to bind (Maryanski et al., *J. Exp. Med.*, 167, 1391–405 (1988); Adorini et al., *Nature*, 342, 800–3 (1989)). In the present case, if the culture medium or the transfectant itself were the source of the putative peptide needed for allostimulation, then cultured cells would have had ample time to form the stimulatory peptide-MHC molecule complexes prior to the introduction of the potentially competing PCC 81-104 peptide.

Figure 2B:
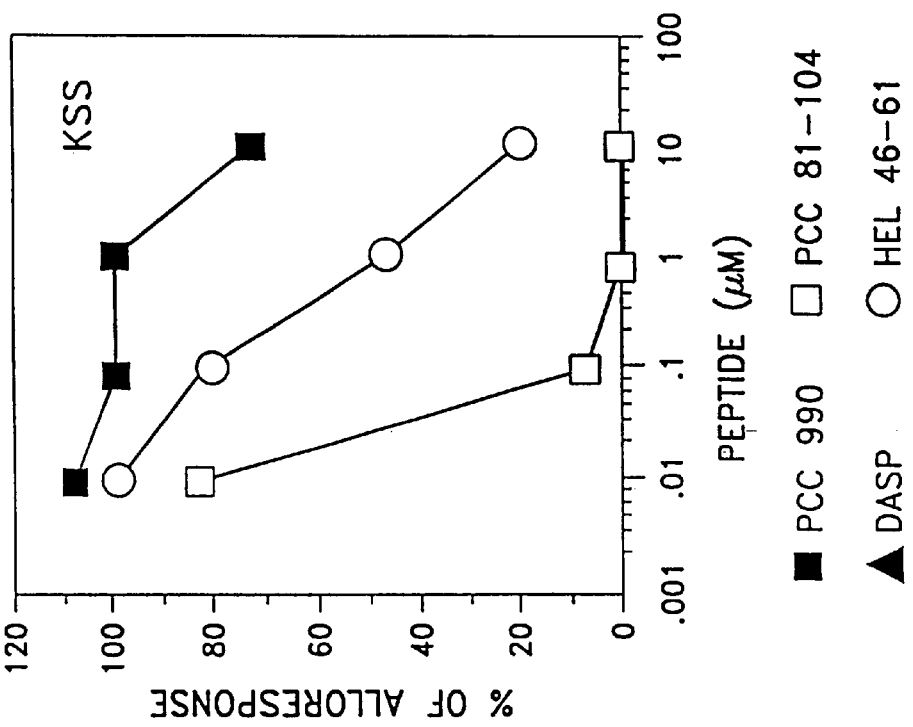
FIG. 2B demonstrates the response of 3C6 Th1 cells to the peptides PCC 81-104, PCC 81-104 [99Q], and DASP presented by an L cell transfectant expressing MHC molecules with wild-type Eβ$^k$ kkk chains as measured by percent of maximal stimulation of IL-2 production.
Figure 2C:
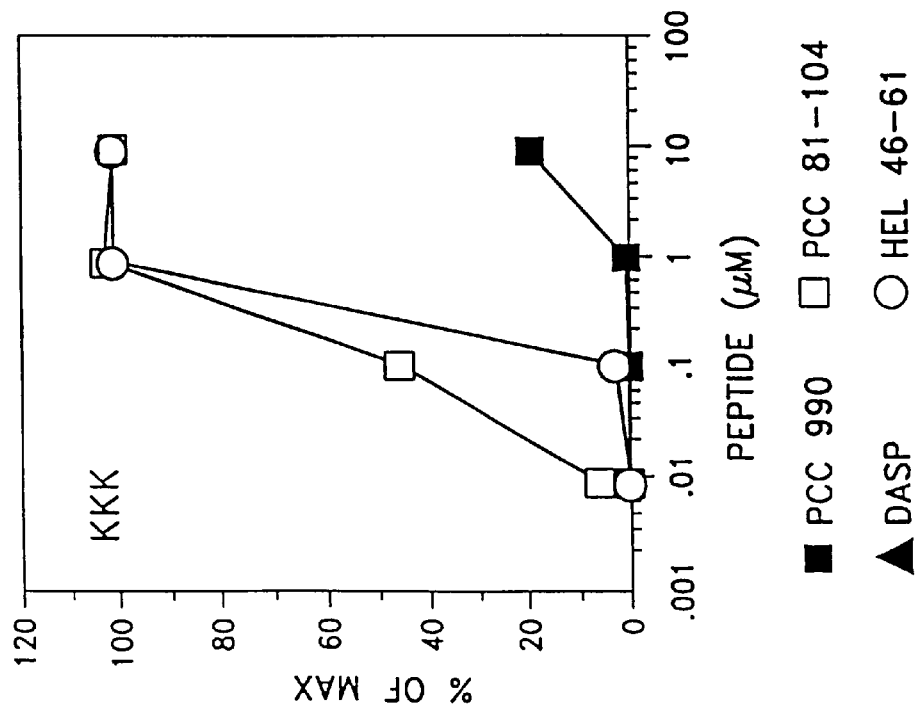
FIG. 2C demonstrates the response of 3C6 Th1 cells to the peptides PCC 81-104, PCC 81-104 [99Q], and DASP presented by an L cell transfectant expressing MHC molecules with kss Eβ chains as measured by percent of stimulation of IL-2 production in the absence of added peptide.

Possible competition for peptide-MHC binding by PCC 81-104 was investigated by examining and comparing the effects of peptides PCC 81-104, PCC [99Q], HEL 46-61, and DASP on 3C6 Th1 alloreactive stimulation of IL-2 production. All peptides with the exception of DASP were able to bind the MHC molecule with kss chains to a similar extent as the inhibitory PCC 81-104 peptide (FIG. 2A). Despite this similarity in MHC molecule binding, the peptides varied over two to three orders of magnitude in their ability to stimulate production of IL-2 in 3C6 Th1 cells when presented by the wild-type $E\alpha E\beta^k$ molecule (FIG. 2B). Whereas comparable results were obtained with PCC 81-104 and DASP, PCC [99Q] demonstrated impaired ability to stimulate IL-2 production. These data confirm the assignment of position 99 as a key epitopic residue in the PCC determinant (Hansburg et al., *J. Immunol.*, 131, 319–24 (1983); Fox et al., *J. Immunol.*, 139, 1578–88 (1987); Jorgensen et al., *Nature*, 355, 224–30 (1992)), and show that the change at this position from lysine to glutamine affects TCR-dependent recognition, and not MHC molecule binding. Moreover, the ability of the peptides to inhibit the 3C6 Th1 alloresponse to MHC molecules with kss chains was directly related to their capacity to stimulate the clone in the context of the wild-type $E\alpha E\beta^k$ molecule (FIG. 2C). Namely, PCC 81-104 peptide, which showed the greatest ability to stimulate IL-2 production when presented by wild-type MHC molecules also showed the greatest ability to inhibit the 3C6 Th1 alloresponse to the MHC molecules with kss chains. Similarly, PCC [99Q] peptide, which showed the least ability to stimulate IL-2 production when presented by wild-type MHC molecules also showed the least ability to inhibit the 3C6 Th1 alloresponse to MHC molecules with kss chains. Thus, it is the fine specificity of the 3C6 Th1 TCR for the peptide, and not the ability of the peptide to bind to the mutant MHC molecule which dictates capacity to inhibit alloantigen-stimulated IL-2 production. This argues against competition between peptides for MHC binding as the cause of peptide inhibition of alloreactivity.

Figure 3B:
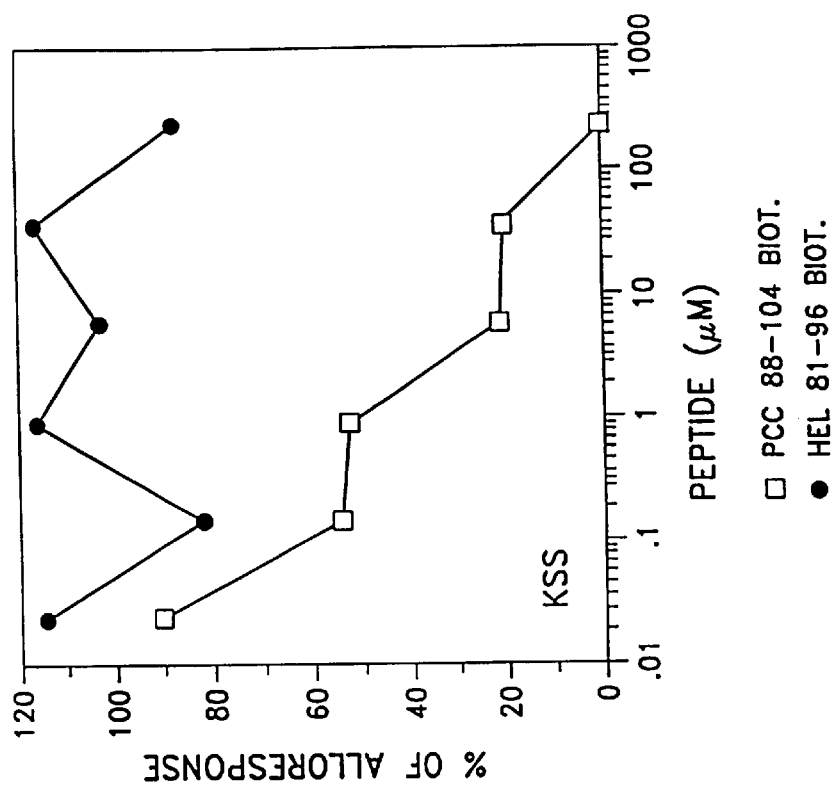
FIG. 3B demonstrates the effect of the biotinylated peptides PCC 88-104 and HEL 81-96 on alloreactive stimulation of IL-2 production by an L cell transfectant expressing MHC molecules with kss Eβ chains. Data are expressed as percent of IL-2 production obtained in the absence of added peptide.
Figure 3A:
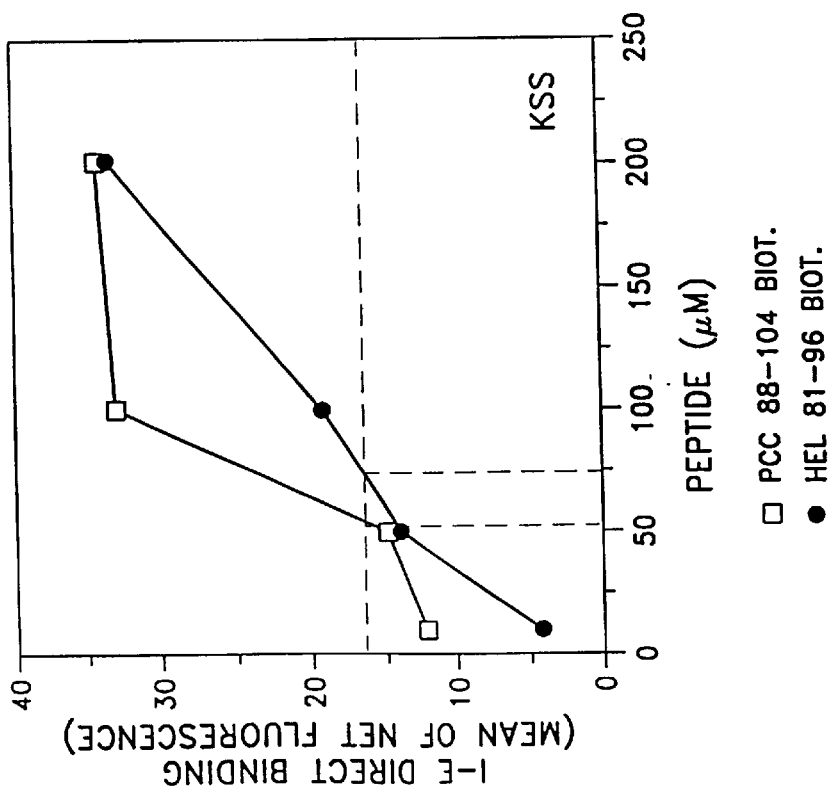
FIG. 3A demonstrates direct binding of the biotinylated peptides PCC 88-104 and HEL 81-96 to an L cell transfectant expressing MHC molecules with kss Eβ chains. Data are expressed as mean net fluorescence.

Additional experiments using an unrelated hen egg lysozyme (HEL 81-96) instead of PCC peptide support this conclusion (FIG. 3). Although HEL 81-96 bound well to the MHC molecules with kss chains (FIG. 3A), this peptide, like PCC [99Q], lacked ability to inhibit alloreactive stimulation of IL-2 production in 3C6 Th1 cells (FIG. 3B).

Example 3

This example confirms that the PCC peptide-mediated inhibition of alloreactive stimulation of IL-2 production in 3C6 Th1 cells demonstrated in Example 1 cannot be explained by high-dose suppression.

Mouse Th1 clones including 3C6 Th1 show a characteristic decline in antigen-stimulated proliferation as the concentration of offered antigen is increased to high levels (Matis et al., *Proc. Natl. Acad. Sci. USA*, 80, 6019–23 (1983a); Suzuki et al., *J. Immunol.*, 140, 1359–65 (1988)). This high-dose suppression appears to be related to prolonged or repetitive engagement of the TCR. The possibility that the low apparent response of 3C6 Th1 cells to MHC molecules with kss chains was due to a high level of allostimulation, and was attenuated by additional PCC peptide-MHC molecule complexes was investigated.

Figure 4B:
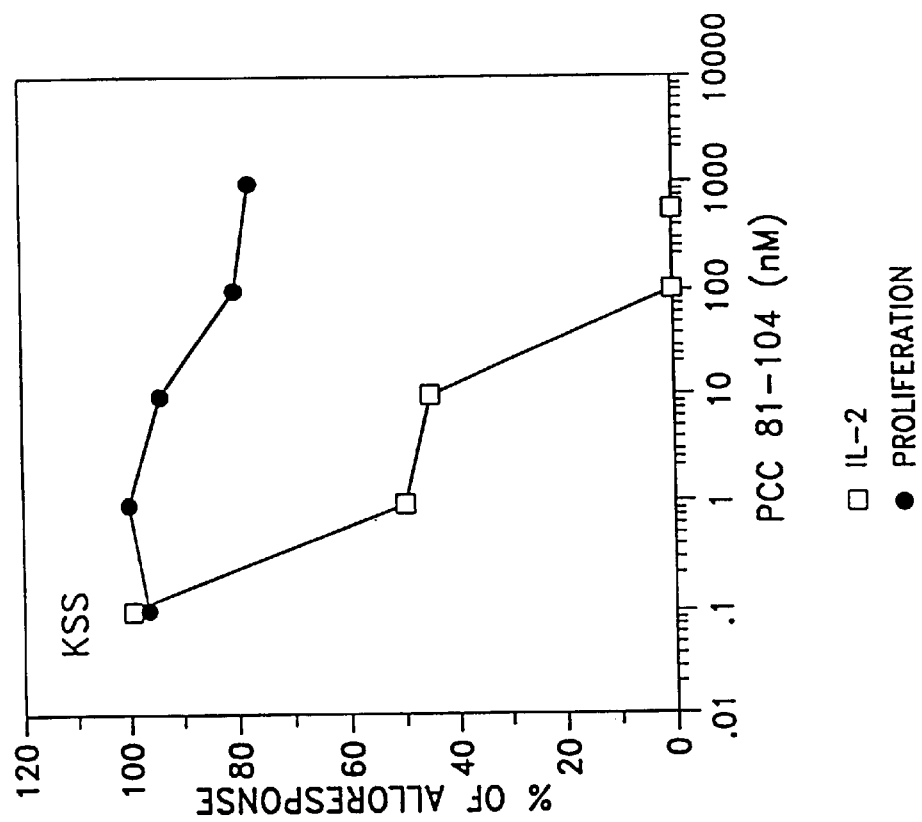
FIG. 4B demonstrates the response of 3C6 Th1 cells to PCC 81-104 presented by an L cell transfectant expressing MHC molecules with kss Eβ chains as measured by percent of IL-2 production and proliferation obtained in the absence of added peptide.
Figure 4A:
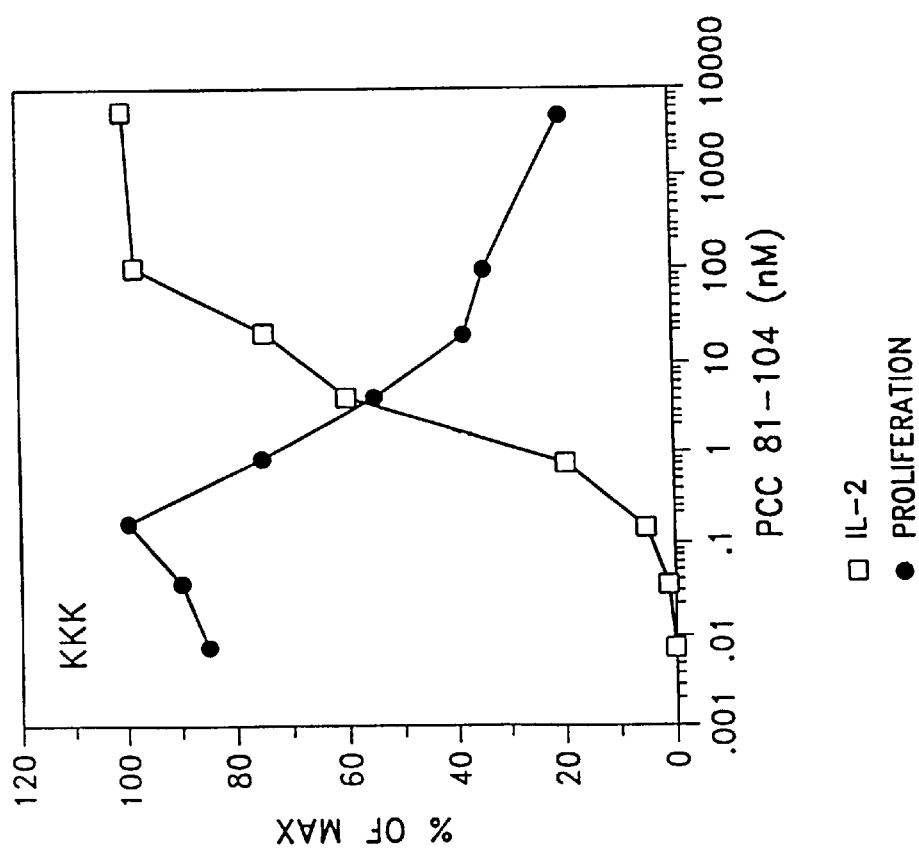
FIG. 4A demonstrates the response of 3C6 Th1 cells to PCC 81-104 presented by an L cell transfectant expressing MHC molecules with wild-type kkk Eβ chains as measured by percent stimulation of IL-2 production and proliferation.

Upon stimulation of 3C6 Th1 cells with wild-type MHC molecules plus PCC 81-104 peptide, high-dose suppression of proliferation was observed, whereas stimulation of IL-2 production increased with increasing amounts of added peptide (FIG. 4A). The 3C6 Th1 cells showed a different phenotype upon stimulation with MHC molecules possessing kss chains plus PCC 81-104 peptide (FIG. 4B). In this case, increasing amounts of added PCC peptide decreased IL-2 accumulation in a dose-dependent fashion and only marginally diminished proliferation. Furthermore, addition of anti-EαEβ mAb to 3C6 Th1 stimulated with MHC molecules possessing kss chains did not result in augmentation of IL-2 production in the absence of PCC peptide (data not shown), which would be expected due to reduction in receptor engagement caused by antibody addition if the alloresponse were in the high-dose suppression range. Thus, these results verify that the inhibitory effect of peptide PCC 81-104 is not due to excessive TCR-dependent stimulation of 3C6 Th1.

Example 4

This example confirms that the PCC peptide-mediated inhibition of alloreactive stimulation of IL-2 production in 3C6 Th1 cells demonstrated in Example 1 is specific for this effector response and does not inhibit all TCR-dependent signalling.

Figure 5A:
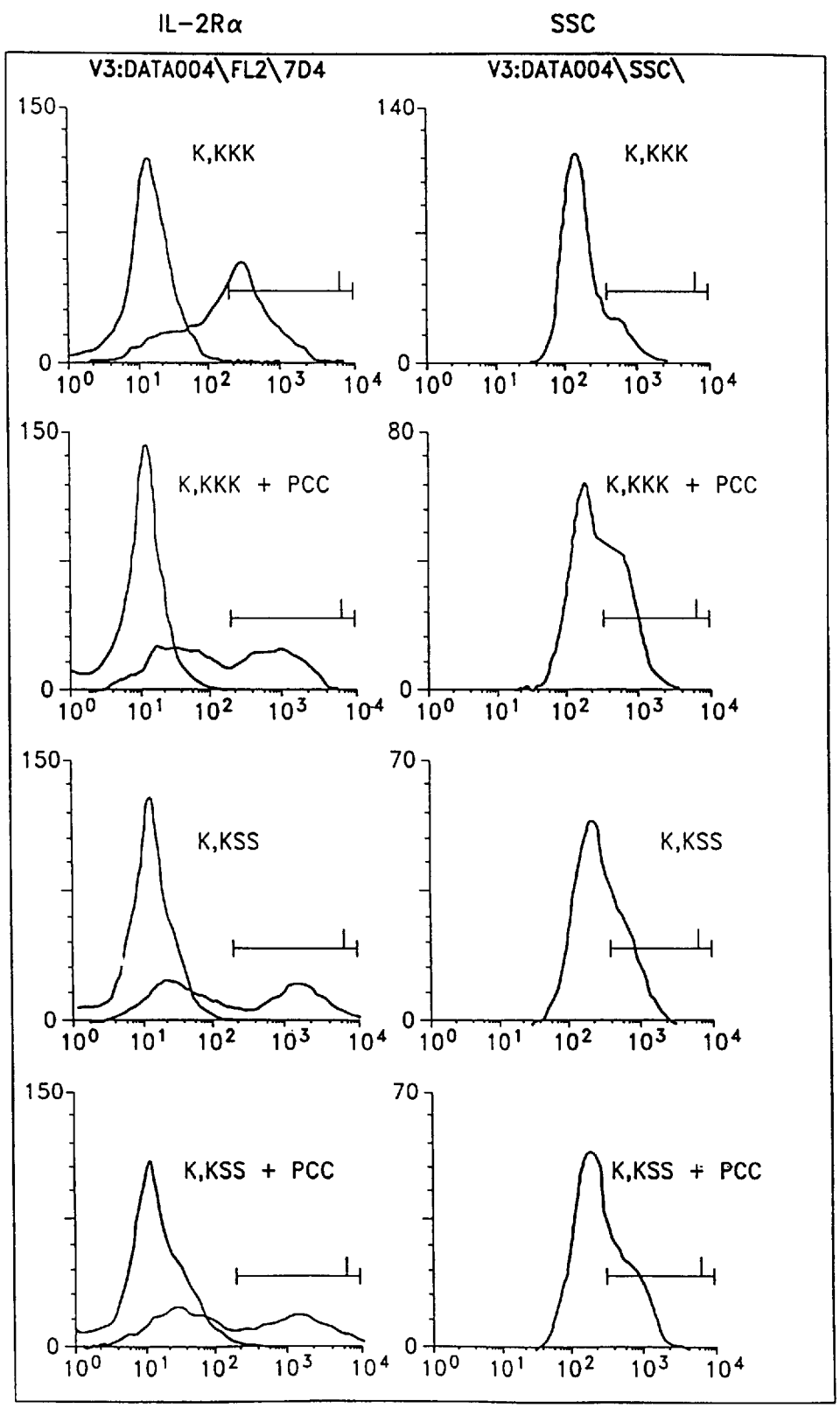
FIG. 5A demonstrates two-color flow cytometry profiles of 3C6 cells co-cultured for 24 hours with transfected L cells expressing either MHC molecules with wild-type kkk or mutant kss Eβ chains. The left panel shows anti-IL-2 receptor a chain (7D4) staining of Thy-1 (G7)-negative and positive cells. The Thy-1 protein is a marker for T lymphocytic 3C6 Th1 cells. The right panel shows size (SSC) of the G7-positive or 3C6 Th1 cells. The Eβ chain of the MHC molecule expressed by the L cell as well as the presence or absence of PCC 81-104 are indicated in each panel.
Figure 5B:
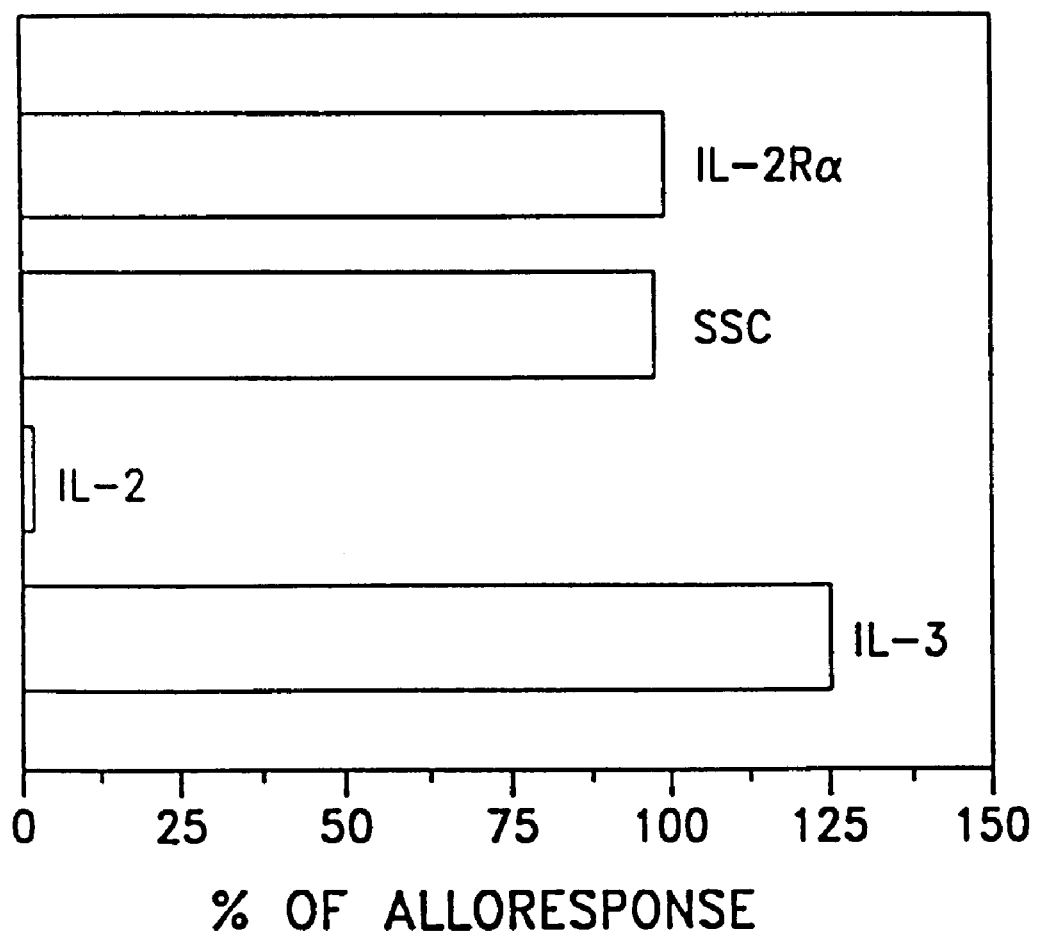
FIG. 5B demonstrates the relative change in IL-2Rα expression (IL-2Rα) for cells included in the gate 1 subset of Thy-1$^+$ cells in FIG. 5A (i.e., 3C6 Th1 cells), in size (SSC), in IL-2 production (IL-2), and in IL-3 production (IL-3). While IL-2Rα was determined by comparing cultures with transfectants expressing MHC molecules with kss Eβ chains in the absence and presence of PCC 81-104, SSC was calculated as change in percent of cells in gate 1 of the right panel of FIG. 5A by comparing co-cultures with transfectants expressing the kss Eβ chain in the absence and presence of PCC 81-104, and IL-2 and IL-3 production were determined by comparing relative production in co-cultures with transfectants expressing the kss Eβ chain in the absence and presence of PCC 81-104.
Figure 5C:
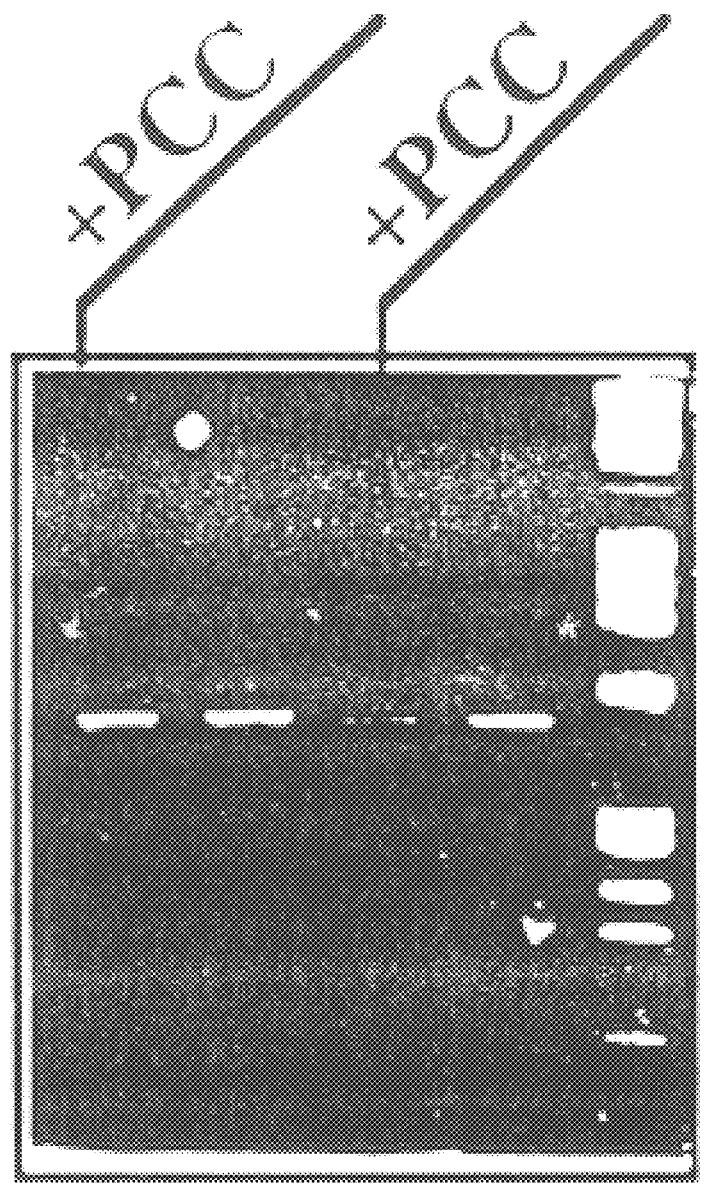

Several experiments were performed to determine if TCR-dependent signal transduction occurs when 3C6 Th1 cells re exposed to MHC molecules with kss chains plus PCC 81-104 peptide. Even though PCC 81-104 peptide addition inhibited alloreactive stimulation of IL-2 accumulation (IL-2) in 3C6 Th1 cells, TCR-dependent alloreactive IL-2Rα production (IL-2Rα), cell size enlargement (SSC) and IL-3 production (IL-3) proceeded as they did in the absence of added PCC peptide (data shown pictorially in FIG. 5A and quantitatively in FIG. 5B). Thus, 3C6 Th1 continued to receive biologically active signals through the TCR under conditions in which the IL-2 alloresponse was abrogated. This validates that the activity of complexes of PCC 81-104 with mutant MHC molecules possessing kss chains in inhibiting production of IL-2 did not result from the elimination of effective TCR occupancy by the agonist alloantigen (FIGS. 5C and 5D).

The decrease in IL-2 in 3C6 Th1 cells upon presentation of peptide by MHC molecules with kss chains was not the result of increased IL-2 consumption by proliferating cells, but was due to a decrease in steady-state IL-2 mRNA levels. This decrease was specific for IL-2 mRNA, as IL-3 mRNA levels were similar in the presence or absence of added PCC peptide.

Example 5

This example supports that the PCC peptide-mediated inhibition of alloreactive stimulation of IL-2 production in 3C6 Th1 cells demonstrated in Example 1 may arise from interference with selective synergy between co-stimulatory and TCR-generated signals, and not from a reduction in the number of TCR available for alloantigen recognition due to engagement of TCR by PCC peptide-mutant MHC molecule complexes and failure to contribute to TCR-dependent signal generation.

Figure 6:
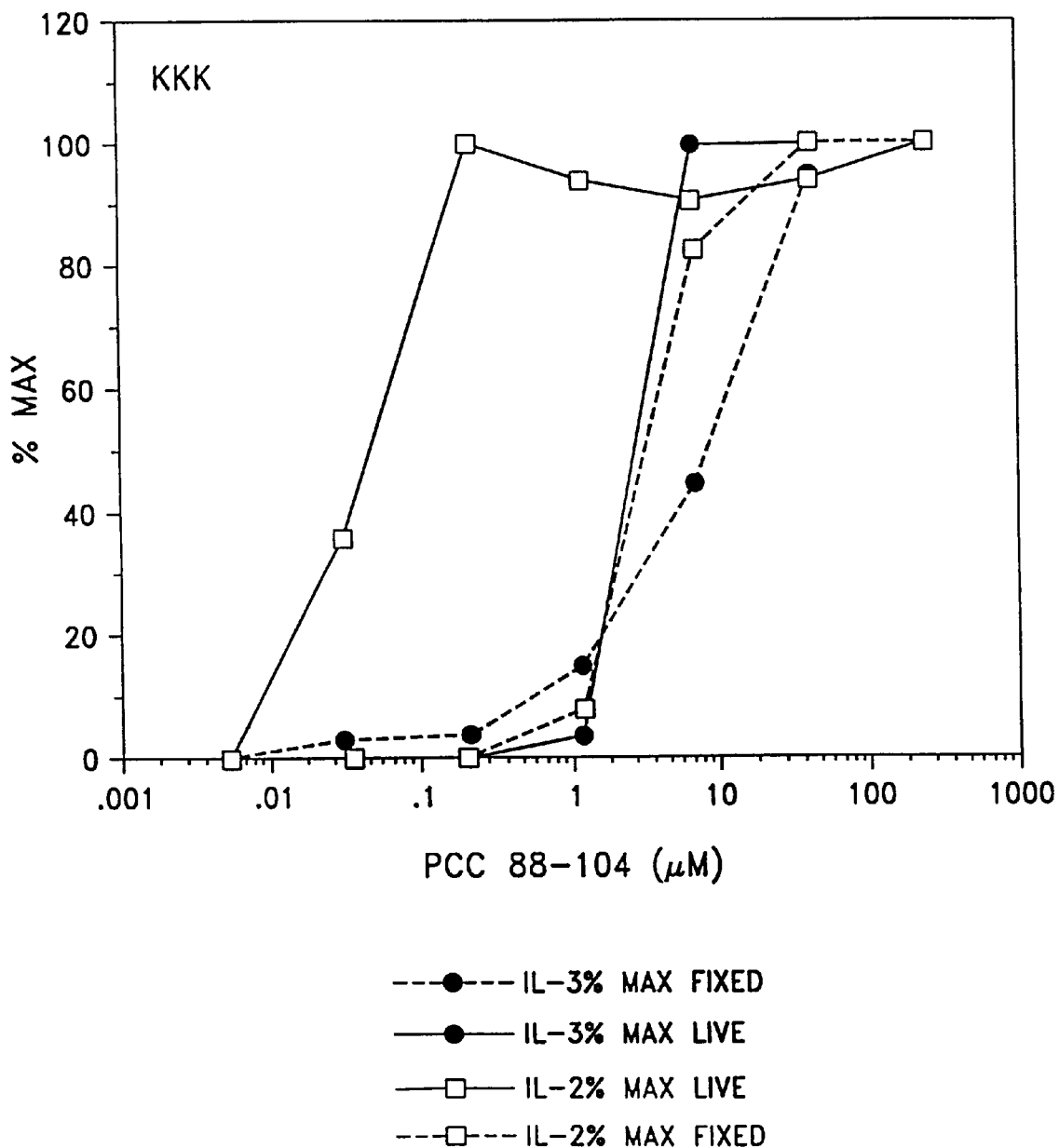
FIG. 6 sets forth the antigen dose-response patterns of stimulated IL-2 and IL-3 production by 3C6 Th1 cells to peptide presented on live or fixed L cell transfectants expressing MHC molecules with wild-type Eβ$^k$ kkk chains. Results are expressed as the percent of the maximum IL-2 or IL-3 response, respectively, obtained with live or fixed APC.

The inhibitory effect of PCC peptide on the 3C6 Th1 alloresponse is not due to inhibition of alloantigen formation or high-dose suppression (Examples 2 and 3). While inhibition is related to receptor engagement by the PCC peptide-mutant MHC molecule complexes (Example 2), it does not result from a blockade of all TCR-dependent signal transduction (Example 4). The further less-likely possibility that the PCC peptide-mutant EαEβ complexes reduced the number of TCR available for alloantigen recognition by engaging the TCR without contributing to signal generation was investigated by examining the relative sensitivity of 3C6 Th1 cells to stimulation of IL-2 and IL-3 production with wild-type MHC molecules plus PCC 81-104 peptide. As can be seen in FIG. 6, 100-fold less peptide was required to attain the same fraction of maximal response for IL-2 production than was needed for IL-3 production. This suggests that IL-3 production requires higher, not lower, TCR occupancy than does IL-2 production. This is the opposite of what would be required to explain selective peptide-MHC molecule complex dependent inhibition of alloantigen-driven IL-2 but not IL-3 production on the basis of differential sensitivity to residual TCR signalling, because at any level of reduced occupancy based on TCR blockade, a greater reduction in IL-3 than IL-2 production should have been seen.

The phenotype of TCR-dependent IL-3 production in the absence of IL-2 production by Th1 clones has been previously reported. Namely, Th1 clones stimulated by peptide-MHC molecule complexes in planar membranes gave significant, though subnormal IL-3 production, whereas IL-2 production was not observed under these conditions (Quill et al., *J. Immunol.*, 138, 3704–12 (1987)). The defect in IL-2 production under these conditions has been attributed to the absence of at least one essential co-stimulatory signal provided by viable APC which is separate and distinguishable from ligand-receptor interactions that affect the occupancy of the TCR or its production of second messengers (Mueller et al., *Ann. Rev. Immunol.*, 7, 445–80 (1989*b*)). The possibility in the present case that the ability of 3C6 Th1 cells to produce IL-2 at low ligand densities with viable APC resulted from a requisite synergy between TCR signalling and co-stimulatory signalling that was not needed for IL-3 gene activation was investigated by comparing the dose-responses for the two cytokines using aldehyde-fixed APC with greatly reduced levels of co-stimulatory signals. As previously reported (Jenkins et al., *J. Exp. Med.*, 165, 302–19 (1987)), the cytokine responses elicited by fixed APC were reduced more than 90% as compared with live APC (data not shown). However, the antigen concentration needed for half-maximal IL-3 responses with fixed APC was only slightly increased (about three-fold) compared to that needed with viable APC, whereas the dose needed for half-maximal IL-2 production with fixed APC increased close to 100-fold to approach that required for IL-3 (FIG. 6).

These results confirm that peptide inhibition of alloreactive stimulation of IL-2 production in 3C6 Th1 cells is the result of a necessary synergy between TCR-generated signals and co-stimulatory signals.

Example 6

This example further validates a role for co-stimulatory signalling in the PCC peptide-mediated inhibition of alloreactive stimulation of IL-2 production in 3C6 Th1 cells demonstrated in Example 1.

Cytokine responses to viable and fixed cells described in Example 5 confirm that the selective inhibition by PCC-mutant MHC molecule complexes of alloantigen-stimulated IL-2 production may reflect interference with the generation of, or response to, co-stimulation in 3C6 Th1 cells. The L cell transfectant shown in FIG. 6 which expresses wild-type MHC molecules also constitutively expresses the membrane protein B7 (Razi-Wolf et al., *Proc. Natl. Acad. Sci. USA*, 89, 4210–14 (1992)), which is a ligand for the CD28 co-stimulatory pathway. The capacity to observe low but detectable IL-2 production using this L cell transfectant as an APC after it has been fixed seems to relate to a low level of residual co-stimulation that is mediated by pre-existing B7 protein present on the fixed cells. Since experiments with purified peptide-MHC molecule complexes in planar membranes demonstrate that Th1 clones do not produce IL-2 in response to peptide-MHC molecule ligands in the absence of co-stimulatory signals (Quill et al., *J. Immunol.*, 138, 3704–12 (1987)), alloantigen-mediated 3C6 Th1 IL-2 production in the complete absence of co-stimulation could not be investigated. However, since T cell hybridomas do produce IL-2 in the absence of co-stimulatory signals (Watts et al., *Proc. Natl. Acad. Sci. USA*, 81, 7564–8 (1984)), the effect of PCC peptide on the alloreactive stimulation of IL-2 production of a T cell hybridoma bearing the same TCR as 3C6 Th1 was investigated. This T cell hybridoma was derived by fusion of a TCR-chain negative T lymphoma cell with the 3C6 Th1 clone, and is characterized by a peptide and alloantigenic response profile that is indistinguishable from the 3C6 Th1 clone (data not shown).

Unlike the 3C6 Th1 clone, in the presence of viable APC, the hybridoma did not exhibit a substantial difference in its IL-2 and IL-3 dose-responses to PCC 81-104 antigen presented by wild-type MHC molecules with kkk chains (FIG. 7A). Instead, the hybridoma responded to viable APC almost precisely as did the 3C6 Th1 clone to fixed APC lacking almost all co-stimulatory activity. This suggests that co-stimulation related signals do not play a major role in IL-2 production by the hybridoma. The results also support that the difference in the cytokine dose-responses to antigen presented by fixed or viable cells seen for 3C6 Th1 was the result of the essential contribution of co-stimulation to the IL-2 response of normal T cells. The alloantigen-stimulated IL-2 response of the hybridoma was not decreased by addition of PCC peptide (FIG. 7B), which further supports that the inhibitory effect of PCC peptide on the alloresponse of the 3C6 Th1 cells was due to interference with exogenously provided co-stimulation.

These data also confirm that the complexes of PCC peptide with the MHC molecules possessing kss chains are not complete antagonists of, but are actually weak agonists for, TCR signal generation, since at high antigen concentrations they could clearly elicit an effector response from the hybridoma, as evidenced by increased IL-3 production. Given the slight dose-response advantage seen for IL-2 production over IL-3 production upon peptide presentation by wild-type MHC molecules (FIG. 7A), it is somewhat surprising that a stimulation of IL-2 production was not observed with antigen presented by MHC molecules with kss chains. However, this may be due to generation of qualitatively different signals upon TCR engagement of wild-type MHC-PCC peptide complexes as compared with mutant MHC-PCC peptide ligand, and the mutant MHC-PCC peptide ligand may simply be inadequate to evoke IL-2 responses in the hybridoma. Alternatively, even though co-stimulation is not required for IL-2 production by hybridomas, it modestly increases such responses and thus could explain the slight dose-response advantage seen for IL-2 compared to IL-3.

Example 7

This example supports that the PCC peptide-mediated inhibition of alloreactive stimulation of IL-2 production in 3C6 Th1 cells demonstrated in Example 1 either involves interference with co-stimulatory signal transduction within the T cell or the disruption of a crucial distinct costimulatory pathway.

Interaction of the CD28 molecule on T cells with the B7 membrane protein on APC appears to activate a major co-stimulatory pathway involved in regulating IL-2 production (Linsley et al., *J. Exp. Med.*, 173, 721–30 (1991); Koulova et al., *J. Exp. Med.*, 173, 759–62 (1991); Freeman et al., *J. Exp. Med.*, 174, 625–31 (1991); Gimmi et al., *Proc. Natl. Acad. Sci. USA*, 88, 6575–9 (1991); Reiser et al., *Proc. Natl. Acad. Sci. USA*, 89, 271–5 (1992); Vandenberghe et al., *J. Exp. Med.*, 175, 951–60 (1992)). Antibody to the CD28 molecule on mouse or human T cells can modulate the cytokine response of such cells to TCR stimulation (Damle et al., *J. Immunol.*, 140, 1753–1761 (1988); Ledbetter et al., *Blood*, 75, 1531–9 (1990); Harding et al., *Nature*, 356, 607–9 (1992)), presumably by altering delivery of a critical co-stimulatory signal. Because the observations described herein suggested that the PCC-induced downregulation of IL-2 production was related to the necessity of co-stimulation for IL-2 allostimulation, the role of CD28 in IL-2 responses of the 3C6 Th1 clone and the possibility that antibody-mediated activation of the CD28 signalling pathway might counteract the inhibitory effect of the peptide-mutant MHC molecule complexes was examined.

Figure 8A:
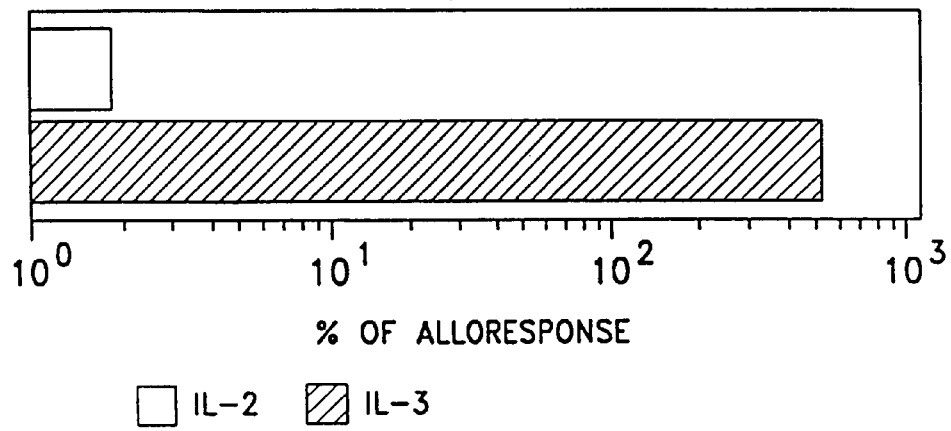
FIG. 8A demonstrates stimulation of IL-2 and IL-3 production in 3C6 Th1 cells by an L cell transfectant expressing MHC molecules with kss Eβ chains in the presence of monoclonal antibody (mAb) directed against CD28 (1:250 dilution of ascites). Data are expressed as percent of the response obtained in the absence of the anti-CD28 mAb.

Inclusion of soluble anti-CD28 in a co-culture of 3C6 Th1 cells and the L cell transfectant expressing MHC molecules with kss chains resulted in almost complete inhibition of IL-2 production, and did not decrease IL-3 production (FIG. 8A). This is consistent with prior data on the effect of soluble anti-CD28 on IL-2 secretion in response to alloantigen (Damle et al., *J. Immunol.*, 140, 1753–1761 (1988)) and replicates the phenotype seen upon addition of PCC peptide to similar cultures. The ability of soluble anti-CD28 to inhibit alloreactive stimulated IL-2 production by the 3C6 Th1 clone supports a critical role for CD28 in co-stimulation of IL-2 production, presumably via interaction with the B7 surface protein present on the transfected L cells.

Figure 8B:
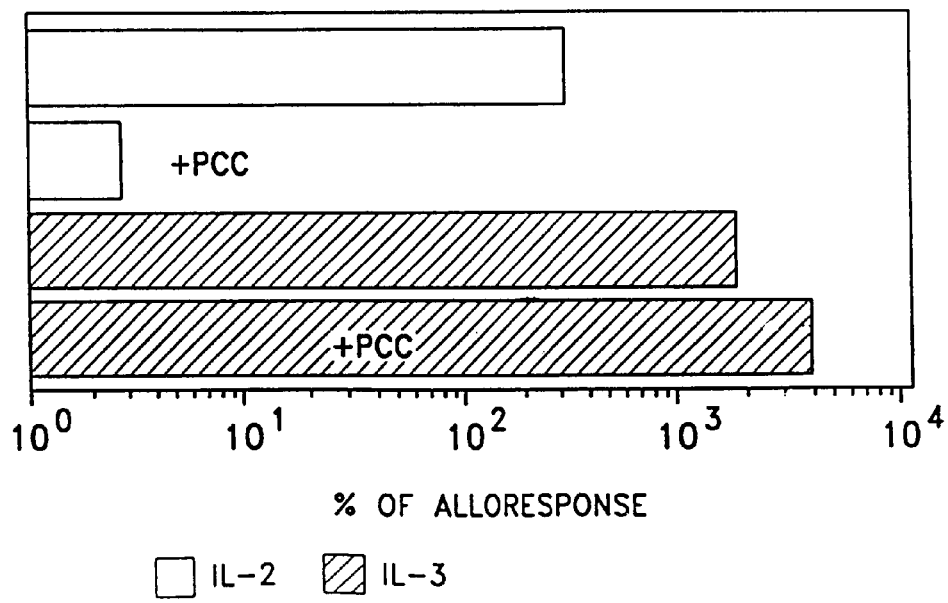
FIG. 8B demonstrates the effect of antibody-mediated cross-linking of CD28 on stimulation of IL-2 and IL-3 production in 3C6 Th1 cells by an L cell transfectant expressing MHC molecules with kss Eβ chains in the absence and presence of 1 μM PCC 81-104 peptide. Data are expressed as percent of the response obtained in the absence of both the mAb and the PCC peptide.

Antibody-mediated cross-linking of CD28 resulted in a small increase in IL-3 production consistent with the previously described ability of co-stimulation to augment this response without being required for it. Antibody-mediated cross-linking of CD28 nullified the inhibitory effect of soluble anti-CD28 on alloreactive stimulation of IL-2 production in 3C6 Th1 cells. Thus, even though results obtained with soluble mAb verified the necessity of CD28-dependent signalling for IL-2 production by 3C6 Th1 cells, stimulation of this pathway by cross-linking CD28 did not reverse the inhibition of IL-2 secretion mediated by PCC peptide addition (FIG. 8B). These results confirm that peptide-mediated inhibition of IL-2 secretion involves either interference with effective CD28 co-stimulatory signal transduction within the T cell or disruption of a crucial co-stimulatory pathway distinct from that evoked by CD28 aggregation, such as a pathway involving heat-stable antigen (Kay et al., *J. Immunol.*, 145, 1952–59 (1990)), which has recently been suggested as another APC-expressed molecule regulating IL-2 production (Liu et al., *J. Exp. Med.*, 175, 437–45 (1992)).

All of the references cited herein are hereby incorporated in their entireties by reference.

While this invention has been described with an emphasis upon a preferred embodiment, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of modulating a T cell effector response by contacting T cells with an altered T cell receptor ligand that substantially inhibits at least one T cell effector response while not substantially inhibiting at least one other T cell effector response, said altered TCR ligand comprising an MHC molecule and a peptide, wherein the MHC molecule is altered by mutation or the peptide is altered by the replacement of at least one residue.

2. A method of modulating a T cell effector response according to claim 1 by contacting T cells with said altered T cell receptor ligand whereby said altered T cell receptor ligand inhibits a co-stimulation dependent T cell effector response evoked by fully activating peptide-MHC molecule complexes available to responding T cells and said altered T cell receptor ligand does not block co-stimulation independent T cell effector responses under the same conditions.

3. A method of modulating a T cell effector response according to claim 1 by contacting T cells with said altered T cell receptor whereby said altered T cell receptor ligand actively and selectively inhibits certain T cell effector activities evoked by activating peptide-MHC molecule complexes, when said altered ligand and said activating peptide-MHC molecule complexes are both available to responding T cells, without inhibiting all other T cell effector activities and without inhibiting all T cell signaling.

4. A method of modulating a T cell effector response according to the method of claim 1 by contacting T cells with an altered T cell receptor ligand, whereby said altered T cell receptor ligand actively and selectively inhibits certain T cell effector activities in a T cell receptor-specific manner evoked by unaltered activating peptide-MHC molecule complexes when said altered ligand and said activating peptide-MHC molecule complexes are both available to responding T cells, while stimulating one or more other T cell effector activities.

5. A method of modulating the immune response of an animal by administering thereto an altered T cell receptor ligand, or altered component thereof, said altered T cell receptor ligand comprising as components an MHC molecule and a peptide, wherein the MHC molecule is altered by mutation or the peptide is altered by the replacement of at least one amino acid residue, whereby at least one T cell effector response is substantially inhibited while at least one other T cell effector response is not substantially inhibited.

6. A method of modulating the immune response of an animal by administering thereto an altered T cell receptor ligand or altered ligand component thereof, according to the method of claim 5, whereby co-stimulation dependent T cell effector responses evoked by fully activating peptide-MHC molecule complexes available to responding T cells are inhibited and co-stimulation independent T cell effector responses are not blocked under the same conditions.

7. A method of modulating the immune response of an animal by administering thereto an altered T cell receptor ligand or altered component thereof, according to the method of claim 5, whereby said altered T cell receptor ligand, or altered component thereof, actively and selectively inhibits certain T cell effector activities evoked by unaltered activating peptide-MHC molecule complexes and does not inhibit all other T cell effector activities and T cell signaling when said altered ligand and said activating peptide-MHC molecule complexes are both available to responding T cells.

8. A method of modulating the immune response of an animal by administering thereto, according to the method of claim 5, an altered T cell receptor ligand, or altered T cell receptor ligand component thereof, that actively and selectively inhibits certain T cell effector activities in a T cell receptor-specific manner evoked by activating peptide-MHC molecule complexes when said ligand and said activating peptide-MHC molecule complexes are both available to responding T cells, while stimulating one or more other T cell effector activities.

9. A method according to any one of claims 1–8 wherein the MHC molecule of the T cell receptor ligand is a Class I MHC molecule.

10. A method according to any one of claims 1–8 wherein the MHC molecule of the T cell receptor ligand is a Class II MHC molecule.

11. A method according to any one of claims 5–8 wherein the T cell receptor ligand or ligand component is administered to a human being.

* * * * *

UNITED STATES PATENT AND TRADEMARK OFFICE
CERTIFICATE OF CORRECTION

PATENT NO.    : 5,948,409
DATED         : September 7, 1999
INVENTOR(S)   : Ronald N. Gemain, Luigi Racioppi and Franca Ronchese-Le Gros It is certified that error appears in the above-identified patent and that said Letters Patent is hereby corrected as shown below:

[75] Ronald N. Germain, Potomac, Maryland; Luigi Racioppi, Bethesda Maryland; Franca Ronchese-Le Gros, Wellington, New Zealand.

Signed and Sealed this

Seventh Day of August, 2001

*Attest:*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO.   : 5,948,409                                                           Page 1 of 1
DATED        : September 7, 1999
INVENTOR(S)  : Ronald N. Germain, Luigi Racioppi and Franca Ronchese-Le Gros It is certified that error appears in the above-identified patent and that said Letters Patent is hereby corrected as shown below:

Column 21,
Line 8, please delete "t" and add -- T --.

Signed and Sealed this

Twenty-fifth Day of November, 2003

JAMES E. ROGAN
*Director of the United States Patent and Trademark Office*